US008481034B2

(12) United States Patent
Pytowski et al.

(10) Patent No.: US 8,481,034 B2
(45) Date of Patent: Jul. 9, 2013

(54) ANTI-VEGFR-3 ANTIBODY COMPOSITIONS

(75) Inventors: Bronislaw Pytowski, New York, NY (US); Krishnadatt Persaud, South Ozone Park, NY (US); Nathalie Zayek, New York, NY (US)

(73) Assignee: ImClone, LLC, Indianapolis, IN (US)

( * ) Notice: Subject to any disclaimer, the term of this patent is extended or adjusted under 35 U.S.C. 154(b) by 154 days.

(21) Appl. No.: 13/223,344

(22) Filed: Sep. 1, 2011

(65) Prior Publication Data

US 2012/0058126 A1    Mar. 8, 2012

Related U.S. Application Data

(60) Provisional application No. 61/380,432, filed on Sep. 7, 2010.

(51) Int. Cl.
*A61K 39/395*    (2006.01)
*C07K 16/18*    (2006.01)

(52) U.S. Cl.
USPC ..................................... 424/143.1; 530/388.1

(58) Field of Classification Search
None
See application file for complete search history.

(56) References Cited

FOREIGN PATENT DOCUMENTS

WO        02/060950 A2    8/2002

OTHER PUBLICATIONS

Persaud, et al., Involvement of the VEGF receptor 3 in tubular morphogenesis demonstrated with a human anti-human VEGFR-3 monoclonal that antagonizes receptor activation by VEGF-C, J. Cell Sci. 117:2745-2756 (2004).
Pytowski, et al., Complete and Specific inhibition of Adult Lymphatic Regeneration by a Novel VEGFR-3 Neutralizing Antibody, J. Nat. Cancer Inst., 97(1):14-21 (2005).
Co, et al., Humanized antibodies for antiviral therapy, Proc. Natl. Acad. Sci. USA 88:2869-2873 (1991).
Goldman, et al., Cooperative and redundant roles of VEGFR-2 and VEGFR-3 signaling in adult lymphangiogenesis, FASEB J. 21(4):1003-1012 (2007).
Harlow and Lane (1988) Antibodies, A Laboratory Manual, Cold Spring Harbor Laboratory Press, Cold Spring Harbor, New York, pp. 567-569, ISBN 0-87969-314-2.
Ho, et al., Site-directed mutagenesis by overlap extension using the polymerase chain reaction, Gene 77:51-59 (1989).
Holash, et al., Inhibitors of growth factor receptors, signaling pathways and angiogenesis as therapeutic molecular agents, Cancer Metastasis Rev. 25(2):243-252 (2006).
Jimenez, et al., Generation of a recombinant fully human bifunctional antibody that neutralizes both vascular endothelial growth factor receptor 2 and 3, Proc. Amer. Assoc. Cancer Res. Abstract 2559, vol. 45 (2004); Available online at: http://www.aacrmeetingabstracts.org/cgi/content/abstract/2004/1/591-a?maxtoshow=&hits=10&RESULTFORMAT=&fulltext=JIMENEZ+&searchid=1&FIRSTINDEX=0&volume=2004&issue=1&resourcetype=HWCIT.
Jimenez, et al., A recombinant, fully human, bispecific antibody neutralizes the biological activities mediated by both vascular endothelial growth factor receptors 2 and 3, Mol Cancer Ther. 4(3):427-434. (2005).
Kabat, et al., Sequences of Proteins of Immunological Interest, Fifth Edition, U. S. Department of Health and Human Services, NIH publication No. 91, 3242 (1991).
Laakkonen, et al., Vascular Endothelial Growth Factor Receptor 3 Is Involved in Tumor Angiogenesis and Growth, Cancer Res. 67(2):593-599 (2007).
Nilsson, et al., VEGF receptor 2/-3 heterodimers detected in situ by proximity ligation on angiogenic sprouts, EMBO J. 29(8):1377-1388 (2010).
Pajusola, et. al., FLT4 Receptor Tyrosine Kinase Contains Seven Immunoglobulin-like Loops and Is Expressed in Multiple Human Tissues and Cell Lines, Cancer Res. 52:5738-5743 (1992).
Persaud, et al., Generation and characterization of monoclonal antibodies that antagonize the binding of VEGF-C to VEGFR-3 (Flt-4), AACR Meeting Abstract 247, European J. Can., 38(Suppl 7):78-78 (2002).
Remington: The Science and Practice of Pharmacy, 19th ed., vol. II, Part 7, pp. 1447-1676 (1995), A. Gennaro et al., Mack Publishing Co.
Roberts, et al., Inhibition of VEGFR-3 Activation with the Antagonistic Antibody More Potently Suppresses Lymph Node and Distant Metastases than Inactivation of VEGFR-2, Cancer Res., 66(5):2650-2657 (2006).
Wu, et al., Humanization of a Murine Monoclonal Antibody by Simultaneous Optimization of Framework and CDR Residues, J. Mol. Biol. 294:151-162 (1999).
Zhang, et al., The VEGFR-3 Receptor Participates in Kaposi's Sarcoma Associated Virus (KSHV) / Human Herpes Virus 8 (HHV-8) Infection of Endothelial Cells, ASH meeting Abstract 993, Blood 102(11):279a (2003).
Zhang, et al., Kaposi's Sarcoma Associated Virus Envelope Glycoprotein B Induces Endothelial Cell Migration and Proliferation by Activation of VEGFR-3 through Integrin a3beta1, ASH meeting Abstract 417, Blood 102(11): 122a-123a (2003).
Zhang, et al., Kaposi's Sarcoma-associated Herpesvirus Activation of Vascular Endothelial Growth Factor Receptor 3 Alters Endothelial Function and Enhances Infection, J Biol Chem. 280(28):26216-26224 (2005).
Zhu, et al., Inhibition of Vascular Endothelial Growth Factor-induced Receptor Activation with Anti-Kinase Insert Domain-containing Receptor Single-Chain Antibodies from a Phage Display Library, Cancer Res. 58:3209-3214 (1998).

*Primary Examiner* — Ruixiang Li
(74) *Attorney, Agent, or Firm* — Nicole S. Woods; Averie K. Hason

(57)    ABSTRACT

The present invention provides anti-VEGFR-3 monoclonal antibodies, pharmaceutical compositions containing said antibodies and uses of said antibodies in the treatment of disease.

6 Claims, No Drawings

US 8,481,034 B2

ANTI-VEGFR-3 ANTIBODY COMPOSITIONS

This application claims priority to U.S. provisional application No. 61/380,432 filed 7, Sep. 2010.

This invention is directed to antibodies that bind specifically to Vascular Endothelial Growth Factor Receptor-3 (VEGFR-3), particularly provided herein are amino acid and nucleic acid sequences of anti-VEGFR-3 antibodies, pharmaceutical compositions, and uses of said antibodies in methods of treating a medical condition mediated by VEGFR-3.

Endothelial cell specific growth factors and receptors are believed to be primarily responsible for the stimulation of endothelial cell growth, differentiation, as well as certain cellular functions. One widely studied family of growth factors comprises Vascular Endothelial Growth Factors (VEGFs).

VEGFR-3 is the only receptor tyrosine kinase (RTK) whose expression in normal adult tissues is largely restricted to the lymphatic endothelium. Nascent VEGF-C and VEGF-D specifically bind to VEGFR-3. Proteolytic cleavage of the N- and C-terminal regions of these proteins liberate mature VEGF-$C_{\Delta N \Delta C}$, and VEGF-$D_{\Delta N \Delta C}$, which acquire increased affinity for VEGFR-3. These ligands activate VEGFR-3 signaling and initiate lymphangiogenesis (i.e. the formation of new lymphatic vessels from pre-existing lymphatic vessels).

The pattern of expression of the ligands for VEGFR-3 suggests their involvement not only in the development and maintenance of the normal vascular system but also in tumor angiogenesis and lymphangiogenesis. Further, VEGFR-3 expression has been detected on blood capillaries within tumors. Thus monoclonal antibodies (mAbs) that inhibit the binding of VEGF-C and/or VEGF-D to VEGFR-3 have the potential to inhibit tumour angiogenesis.

In addition, blocking VEGFR-3 activity has been shown to inhibit VEGF-C-enhanced tumour lymphangiogenesis. In many types of cancer, the first site of metastasis is the lymph nodes and therefore blocking VEGFR-3 has the potential to inhibit tumour metastases.

Persaud, et al., J. Cell Science 117:2745-56 (2004), describes certain properties of a human anti-VEGFR-3 monoclonal antibody, but does not disclose the sequence of any such antibodies nor the epitopes that such antibodies may bind. There remains a need therefore for high affinity anti-VEGFR-3 antibodies that bind novel epitopes within VEGFR-3 and which are able to block ligand binding and receptor activation. There further remains a need for anti-VEGFR-3 antibodies which are able to demonstrate anti-tumour efficacy against a variety of tumour types, without significant negative side effects.

The present invention provides an antibody, or antigen binding portion thereof, that binds to human VEGFR-3 wherein:
 a) the binding of said antibody to human VEGFR-3 is reduced by at least 90% by singly mutating Pro-219 of human VEGFR-3 to Leu; and
 b) the binding of said antibody to human VEGFR-3 is reduced by at least 50% by singly mutating Val-175 of human VEGFR-3 to Ala.

Preferably, the level of binding between the antibody, or antigen-binding fragment thereof, and the human or mutant VEGFR-3 is assayed by expressing the soluble extracellular domain of the human or mutant VEGFR-3 as a fusion protein with alkaline phosphatase and then determining the amount of each fusion protein that is able to bind to the antibody using an alkaline phosphatase chemiluminescence assay.

The invention further provides a pharmaceutical composition comprising an antibody, or antigen binding portion thereof, of the present invention together with a pharmaceutically acceptable carrier, diluent or excipient.

In addition, the invention provides a pharmaceutical composition comprising an antibody, or antigen binding portion thereof, of the present invention together with a pharmaceutically acceptable carrier, diluent or excipient and optionally contains at least one other therapeutic ingredient.

The invention also provides an antibody, or antigen binding portion thereof, of the invention for use as a medicament.

The invention additionally provides an antibody, or antigen binding portion thereof, of the invention for use in the treatment or prevention of ovarian cancer, human erythroleukaemia, head and neck cancer, breast cancer, renal cell carcinoma, pancreatic cancer, lung cancer, colon cancer and lymph node metastases.

The invention further provides a method of treating a cancer selected from the group consisting of ovarian cancer, human erythroleukaemia, head and neck cancer, breast cancer, renal cell carcinoma, pancreatic cancer, lung cancer, colon cancer and lymph node metastases in a mammal, comprising administering to a mammal in need of such treatment an effective amount of an antibody, or antigen binding portion thereof, of the invention.

The invention additionally provides a use of an antibody, or antigen binding portion thereof, in the manufacture of a medicament for the treatment of a cancer selected from the group consisting of ovarian cancer, human erythroleukaemia, head and neck cancer, breast cancer, renal cell carcinoma, pancreatic cancer, lung cancer, colon cancer and lymph node metastases.

The invention also provides an antibody, or antigen binding portion thereof, of the invention in combination with a further anti-cancer agent selected from cisplatin, 5-fluorouracil, leucovorin, oxaliplatin and docetaxel for simultaneous, separate or sequential use in therapy.

The invention additionally provides a method of treating a cancer selected from the group consisting of ovarian cancer, human erythroleukaemia, head and neck cancer, breast cancer, renal cell carcinoma, pancreatic cancer, lung cancer, colon cancer and lymph node metastases in a mammal, comprising administering to a patient in need thereof a therapeutically effective combination of an antibody, or antigen binding portion thereof, of the invention and a further anti-cancer agent selected from cisplatin, 5-fluorouracil, leucovorin, oxaliplatin and docetaxel.

The antibodies of the present invention bind the second immunoglobulin (Ig)-like domain of a mammalian VEGFR-3. The second Ig-like domain of human VEGFR-3 corresponds to residues 138 to 226 of the full length receptor. See, Pajusola, et. al., Cancer Res. 52:5738-5743 (1992).

The term "second Ig-like domain of a mammalian/human/mouse VEGFR-3" (and variations thereof) is intended to encompass naturally occurring forms of the domain (e.g., purified from a cell that expresses the domain under normal conditions) as well as recombinant versions, e.g., encoded by naturally occurring or synthetic point mutants or truncated versions thereof.

The antibodies of the present invention bind an epitope in the second Ig-like domain of human VEGFR-3 wherein P219 is the dominant constituent of the epitope, V175 is a subordinate constituent of the epitope and L221 is a minor constituent of the epitope. (The numbering of these residues is consistent with the full-length human VEGFR-3, as reported in Pajusola, et. al., supra, and EMBL database, accession number X 68203.) This finding is based in part on the observation that including the mutations V175A or P219L or L221V (i.e., substituting the orthologous murine VEGFR-3 residues) in human VEGFR-3 abolishes or significantly reduces the binding of antibodies of the present invention to the mutant human VEGFR-3.

Moreover, the antibodies of the present invention that bind an epitope in human VEGFR-3 (wherein P219 is the dominant constituent of the epitope, V175 is a subordinate constituent of the epitope and L221 is a minor constituent of the epitope) are able to block the binding of the ligand VEGF-C to VEGFR-3 and thus neutralise the activity of the receptor. Accordingly, the present invention provides a novel, neutralising epitope on human VEGFR-3 that allows the production of novel neutralising antibodies to human VEGFR-3, which are able to block the binding of human VEGF-C to the receptor. The invention thus provides an epitope of human VEGFR-3 wherein P219 is the dominant constituent of the epitope, V175 is a subordinate constituent of the epitope and L221 is a minor constituent of the epitope.

The invention also provides an antibody, or antigen-binding portion thereof, that binds an epitope of human VEGFR-3 comprising the amino acid residues P219 and V175. Preferably the invention also provides an antibody, or antigen-binding portion thereof, that binds an epitope of human VEGFR-3 comprising the amino acids P219, V175 and L221. Such an epitope is bound by antibodies of the present invention (e.g. Antibody 1) and therefore the invention also provides an antibody, or antigen-binding portion thereof, that reacts with the same epitope of human VEGFR-3 as an antibody having a light chain comprising the amino acid sequence of SEQ ID NO: 15 and a heavy chain comprising the amino acid sequence of SEQ ID NO: 16. An antibody reacting with the same epitope of human VEGFR-3 as certain antibodies of the present invention (e.g., Antibody 1) would compete for binding to human VEGFR-3 and accordingly the invention also provides an antibody, or antigen-binding portion thereof that competes with an antibody having a light chain comprising the amino acid sequence of SEQ ID NO: 15 and a heavy chain comprising the amino acid sequence of SEQ ID NO: 16 for binding to human VEGFR-3.

Preferably, an antibody of the present invention also binds to a mutant mouse VEGFR-3 having the sequence shown in SEQ ID NO: 20 (which includes the mutation L219P) and a mutant mouse VEGFR-3 having the sequence shown in SEQ ID NO: 21 (which includes the mutation A175V) wherein the binding to the mutant mouse VEGFR-3 having the sequence shown in SEQ ID NO: 20 is increased by more than 50-fold when compared with the binding to wild type mouse VEGFR-3 (SEQ ID NO: 19) and the binding to the mutant mouse VEGFR-3 having the sequence shown in SEQ ID NO: 21 is increased by more than 10-fold when compared with the binding to wild type mouse VEGFR-3.

Preferably the level of binding between the antibody, or antigen-binding fragment thereof, and the wild type mouse or mutant mouse VEGFR-3 is assayed by expressing the soluble extracellular domain of the wild type mouse or mutant mouse VEGFR-3 as a fusion protein with alkaline phosphatase and then determining the amount of each fusion protein that is able to bind to the antibody using an alkaline phosphatase chemiluminescence assay.

Preferably, an antibody of the present invention, or antigen-binding portion thereof, has a high affinity for human VEGFR-3. For example, an antibody, or antigen-binding portion thereof, that has a $K_d$ of between $1 \times 10^{-9}$M and $5.6 \times 10^{-11}$M for human VEGFR-3 as measured by surface plasmon resonance on a BIACORE® 2000 biosensor at 20° C. More preferably the antibody, or antigen-binding portion thereof, has a $K_d$ of between $1 \times 10^{-10}$ M and $5.6 \times 10^{-11}$M for human VEGFR-3 as measured by surface plasmon resonance on a BIACORE® 2000 biosensor at 20° C.

Preferably, the present invention provides an anti-VEGFR-3 antibody, or antigen-binding portion thereof, that inhibits the binding of human VEGF-$C_{\Delta N \Delta C}$ to human VEGFR-3 with an $IC_{50}$ of between 2 nM and 1.3 nM.

Preferably, the present invention provides an anti-VEGFR-3 antibody, or antigen-binding portion thereof, that inhibits the VEGF-$C_{\Delta N \Delta C}$ stimulated mitogenic response with an $IC_{50}$ of between 10 nM and 5 nM. More preferably the antibody, or antigen-binding portion thereof, inhibits the VEGF-$C_{\Delta N \Delta C}$ stimulated mitogenic response with an $IC_{50}$ of between 8 nM and 5 nM, most preferably between 6 nM and 5 nM in an assay as described in Example 5.

Preferably, the present invention provides an antibody, or antigen-binding portion thereof, that binds human VEGFR-3 and which comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2 and HCDR3, wherein LCDR1 comprises the amino sequence of SEQ ID NO: 1, LCDR2 comprises the polypeptide of SEQ ID NO: 2, LCDR3 comprises the polypeptide of SEQ ID NO: 3, HCDR1 comprises the polypeptide of SEQ ID NO: 6, HCDR2 comprises the polypeptide of SEQ ID NO: 7 and HCDR3 comprises the polypeptide of SEQ ID NO: 8.

More preferably, the present invention provides an antibody, or antigen-binding portion thereof, that binds human VEGFR-3 and that comprises an LCVR polypeptide of SEQ ID NO: 5 and an HCVR polypeptide of SEQ ID NO: 10.

More preferably, the present invention provides an antibody, or antigen-binding portion thereof, that binds human VEGFR-3 and that comprises a light chain comprising the polypeptide of SEQ ID NO: 15 and a heavy chain comprising the polypeptide of SEQ ID NO: 16.

Still more preferably, the present invention provides an antibody, or antigen-binding portion thereof, that binds human VEGFR-3 and that comprises two light chains comprising the polypeptide of SEQ ID NO: 15 and two heavy chain comprising the polypeptide of SEQ ID NO: 16.

Preferably, the invention provides an antibody, or antigen-binding portion thereof that competes with an antibody of the invention for binding to human VEGFR-3.

Preferably, the invention provides an antibody, or antigen-binding portion thereof, that is a human antibody.

Preferably, the invention provides an antibody, or antigen-binding portion thereof, that is a human-engineered antibody.

Definitions

The term "antibody" as used herein is intended to refer to monoclonal antibodies which may be fully human antibodies or human engineered antibodies, as well as digestion fragments, specified portions and variants thereof, including antibody mimetics, portions of antibodies that mimic the structure and/or function of an antibody or specified fragment or portion thereof, including single chain antibodies and fragments thereof, that retain the ability to bind to the second Ig-like domain of human VEGFR-3. For example, antibody fragments capable of specifically binding the second Ig-like domain of human VEGFR-3 embraced by the present invention include Fab fragments (e.g., by papain digestion), a Facb fragment (e.g., by plasmin digestion), F(ab')$_2$ fragments (e.g., by pepsin digestion) and disulphide-stabilised variable fragments (dsFv) or single chain variable fragments (scFv) generated by molecular biology techniques. Antibody fragments are also intended to include, e.g., domain deleted antibodies, diabodies and triabodies that retain the ability to bind to the second Ig-like domain of human VEGFR-3.

Antibodies include immunoglobulin molecules comprising four polypeptide chains, two heavy (H) chains and two light (L) chains inter-connected by disulfide bonds. Each heavy chain is comprised of a heavy chain variable region (abbreviated herein as HCVR) and a heavy chain constant region. The heavy chain constant region contains three domains, CH1, CH2 and CH3. Each light chain is comprised of a light chain variable region (abbreviated herein as LCVR) and a light chain constant region. The light chains of antibodies from any vertebrate species can be assigned to one of two clearly distinct types, named kappa (κ) and lambda (λ), based on the amino acid sequences of their constant domains. The expression LCVR, as used herein, is intended to include both the variable regions from kappa-type light chains (Vκ) and the variable regions from lambda-type light chains (Vλ). The light chain constant region is comprised of one domain, CL. The HCVR and LCVR regions include regions of sequence hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1-CDR1-FR2-CDR2-FR3-CDR3-FR4. For purposes of the present invention, the LCVR CDRs are abbreviated LCDR1, LCDR2 and LCDR3, and the HCVR CDRs are abbreviated HCDR1, HCDR2 and HCDR3.

Depending on the amino acid sequence of the constant domain of their heavy chains, antibodies can be assigned to different classes. There are five major classes of intact antibodies: IgA, IgD, IgE, IgG, and IgM. Several of these may be further divided into subclasses (isotypes), e.g., IgG1, IgG2, IgG3, IgG4, IgA, and IgA2. The heavy-chain constant domains that correspond to the different classes of antibodies are called alpha (α), delta (Δ), epsilon (ε), gamma (γ), and mu (μ), respectively. The subunit structures and three-dimensional configurations of different classes of immunoglobulins are well known. The present invention includes antibodies that fall into any of the aforementioned classes or subclasses (isotypes).

As used herein, a "monoclonal antibody" refers to an antibody obtained from a population of substantially homogeneous antibodies, e.g., the individual antibodies comprising the population are substantially identical except for possible naturally occurring mutations or minor post-translational variations that may be present. Monoclonal antibodies are highly specific, being directed against a single antigenic site (also known as determinant or epitope), which as taught herein are contained in the second Ig-like domain of a mammalian VEGFR-3. Furthermore, in contrast to conventional (polyclonal) antibody preparations which typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

As used herein, a "human antibody" refers to antibodies having variable and constant regions corresponding to human germline immunoglobulin sequences (as described in Kabat, et al., (1991) *Sequences of Proteins of Immunological Interest,* 5th Edition, U.S. Department of Health and Human Services, NIH Publication No. 91-3242). The term "human antibody," as used herein, is not intended to include antibodies in which CDR sequences derived from the germline of another mammalian species, such as a mouse, have been grafted onto human framework sequences.

Modifications to the amino acid sequence of Antibody 1 as disclosed herein are included within the scope of the present invention, particularly in connection with improvements in the binding affinity and/or other biological properties of the antibodies. In this context, the term "human engineered antibody," as used herein, refers to additional antibodies that have similar functional properties to Antibody 1 (e.g. the ability to bind human VEGFR-3 at an epitope comprising P219 and V175) and which have framework regions that are substantially human or fully human surrounding CDRs that are derived from Antibody 1. Substantially human frameworks in the context of the present invention are those that have at least 80% sequence identity to the framework regions of Antibody 1. Preferably, such substantially human frameworks have at least about 85%, about 90%, about 95%, or about 99% sequence identity to the framework regions of Antibody 1. Human germline sequences are described in WO 2007/044411. For example, germline light chain frameworks may be selected from the group consisting of: A11, A17, A18, A19, A20, A27, A30, LI, L1I, L12, L2, L5, L15, L6, L8, O12, O2, and O8 and germline heavy chain framework regions may be selected from the group consisting of: VH2-5, VH2-26, VH2-70, VH3-20, VH3-72, VHI-46, VH3-9, VH3-66, VH3-74, VH4-31, VHI-18, VHI-69, VH3-11, VH3-15, VH3-21, VH3-23, VH3-30, VH3-48, VH4-39, VH4-59, and VH5-5I.

Human engineered antibodies derived from Antibody 1 may include deletions from and/or insertions into and/or substitutions of residues within the sequence of Antibody 1. However, the final construct must retain the desired functional characteristics of Antibody 1 (e.g., the ability to bind human VEGFR-3 at an epitope comprising P219 and V175).

Human engineered antibodies having similar functional properties to Antibody 1 can be generated using several different approaches, with each approach starting with Antibody 1 (i.e., an antibody having LCVR and HCVR sequences as shown in SEQ ID NO: 5 and SEQ ID NO: 10 respectively) as a template or parent antibody to make additional antibodies. In a first approach, the CDRs of Antibody 1 are grafted into a different human framework that has a high sequence identity with the framework regions of Antibody 1. The sequence identity of the new framework will generally be at least 80%, at least 85%, at least 90%, at least 95% or at least 99% identical with the corresponding framework in Antibody 1. This grafting may result in a reduction in binding affinity compared to Antibody 1. If this is the case, the framework can be back-mutated to the framework of Antibody 1 at certain positions based on specific criteria published by Queen et al., *Proc. Natl. Acad. Sci. USA* 88, 2869 (1991). The identification of residues to consider for back-mutation may be carried out as follows: When an amino acid falls under any of the following categories, the framework amino acid of the human germline sequence that is being used (acceptor framework) is replaced by a framework amino acid from the framework of Antibody 1 (donor framework):

(a) the amino acid in the human framework region of the acceptor framework is unusual for human frameworks at that position, whereas the corresponding amino acid in Antibody 1 is typical for human frameworks at that position;

(b) the position of the amino acid is immediately adjacent to one of the CDRs; or (c) any side chain atom of a framework amino acid is within about 5-6 angstroms (centre-to-centre) of any atom of a CDR amino acid in a three dimensional immunoglobulin model.

When each of the amino acids in the human framework region of the acceptor framework and the corresponding amino acid in the Antibody 1 framework is unusual for human frameworks at that position, such an amino acid may be replaced by an amino acid typical for human frameworks at that position. These back-mutation criteria enable one to recover the activity of Antibody 1.

In a second approach, human engineered antibodies derived from Antibody 1 which retain the functional properties of Antibody 1, (e.g., the ability to bind human VEGFR-3 at an epitope comprising P219 and V175), can be generated by mutating the CDRs of Antibody 1 (either randomly or in a biased fashion to avoid degeneracy of the amino acid code) whilst retaining the framework regions of Antibody 1. Preferably, the mutations (deletions, insertions and/or substitutions) in the amino acid sequences of the CDRs of human engineered antibodies derived from Antibody 1 are limited to a maximum of three mutations, more preferably two mutations or most preferably a single mutation in the CDR sequences of the human engineered antibody when compared with the CDR sequences of Antibody 1. Where more than one mutation is present, the mutations may be distributed across the CDR sequences in a variety of different ways. For example, all of the mutations may occur in a single CDR sequence (e.g., LCDR1), each mutation may occur in a different CDR sequence or two mutations may be found in one CDR sequence and a third mutation found in another CDR sequence. This results in the creation of a combinatorial library of human engineered antibodies, wherein the CDR sequences are mutated at one or more positions as described above, whilst retaining the framework regions of Antibody 1. The library can be screened for additional variants that have similar or improved functional properties when compared with Antibody 1.

A further approach to generate human engineered antibodies derived from Antibody 1 (and which retain the functional properties of Antibody 1, e.g., the ability to bind human VEGFR-3 at an epitope comprising P219 and V 175) is to combine the two approaches described above and make changes in both the frameworks and the CDRs. In other words, after grafting the CDRs of Antibody 1 into a different framework, specific framework residues may be back-mutated in addition to making changes in the CDRs. The general principle of this methodology is described in Wu et al. (1999), *J. Mol. Biol.* 294: 151-162.

The amino acid changes also may alter post-translational processes of the human engineered antibodies, such as changing the number or position of glycosylation sites.

Substitution variants may be generated by substituting one or more hyper-variable region residues of Antibody 1. One such method for generating substitutional variants is known as affinity maturation using phage display. Several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as disclosed herein.

The assays disclosed herein can be used to screen human engineered antibodies derived from Antibody 1 to identify those antibodies having the in vitro and in vivo functions as disclosed herein.

The antibodies of the present invention may be isolated antibodies. An isolated antibody is substantially free of other cellular material and/or chemicals.

The term "epitope," as used herein, refers to a particular molecular region on the surface of an antigen capable of eliciting an immune response and of binding to the specific antibody produced by such a response. An epitope may be a linear epitope (i.e., composed of contiguous amino acid residues all contained within a single short stretch of sequence) or it may be a conformational epitope (i.e., composed of amino acid residues that are in disparate parts of the linear sequence of the antigen, but which are brought together to form the antibody binding site once the antigen assumes its appropriate secondary and tertiary structure). Typically, an epitope is constituted of a small number (e.g., 2 to 5) of key amino acid residues and disruption of those residues (e.g., by mutation to a different amino acid residue) results in a significant reduction or even complete abolition of the binding between the antigen and the epitope.

Antibodies or antigen-binding fragments thereof that "compete" with the molecules disclosed herein are those that bind human VEGFR-3 at site(s) that are identical to, or overlapping with, the site(s) at which the present molecules bind. Competing human engineered antibodies or antigen-binding fragments thereof can be identified, for example, via an antibody competition assay. For example, a sample of purified or partially purified human VEGFR-3 is bound to a solid support. An antibody of the present invention and a test monoclonal antibody or antigen-binding fragment, with either the test or antibody of the present invention labelled, are then added. If the labelled antibody and the unlabeled antibody bind to separate and discrete sites on VEGFR-3, the labelled antibody will bind to the same level whether or not the suspected competing antibody is present. However, if the sites of interaction are identical or overlapping, the unlabeled antibody will compete, and the amount of labelled antibody bound to the antigen will be lowered. If the unlabelled antibody is present in excess, no labelled antibody will bind. For purposes of the present invention, competing human engineered antibodies or antigen-binding fragments thereof are those that decrease the binding of the present antibodies by about 50%, about 60%, about 70%, about 80%, about 85%, about 90%, about 95%, or about 99%. Details of procedures for carrying out such competition assays are well known in the art and can be found, for example, in Harlow and Lane (1988) *Antibodies, A Laboratory Manual*, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared.

Human VEGFR-3 exists in two forms, which are generated by mRNA transcripts of differing length. The longer transcript encodes a protein containing 65 extra amino acid residues at the C terminus when compared with the protein encoded by the shorter transcript, with the longer protein being the major form detected in tissues. The two variants are identical in their N-terminal extracellular domains. The term "human VEGFR-3", unless otherwise stated, refers to both variants of wild type human VEGFR-3 (i.e., SEQ ID NO: 17 and SEQ ID NO: 18) that are derived from the alternate mRNA transcripts.

The nucleic acid and corresponding amino acid sequences of the LCVR region of Antibody 1 are designated as SEQ ID NOS: 4 and 5 respectively.

The nucleic acid and corresponding amino acid sequences of the HCVR region of Antibody 1 are designated herein as SEQ ID NOS: 9 and 10 respectively.

The nucleic acid and corresponding amino acid sequences of the light chain of Antibody 1 are designated herein as SEQ ID NOS: 11 and 12 respectively. Amino acid residues 1-19 of SEQ ID NO: 12 constitute a secretory sequence useful in expression and extraction of the light chain from various mammalian host cell lines, but which is not present in the mature antibody. The amino acid sequence of the mature light chain of Antibody 1 is designated herein as SEQ ID NO: 15.

The nucleic acid and corresponding amino acid sequences of the heavy chain of Antibody 1 are designated as SEQ ID NOS: 13 and 14 respectively. As in the case of the sequence for the light chain, amino acid residues 1-19 of SEQ ID NO: 14 constitute a secretory sequence useful in expression and extraction of the heavy chain from various mammalian host cell lines, but which is not present in the mature antibody. The amino acid sequence of the mature heavy chain of Antibody 1 is designated herein as SEQ ID NO: 16.

Specificity of an antibody can be determined based on affinity and/or avidity. Affinity, represented by the equilibrium constant for the dissociation of an antigen with an antibody ($K_d$), measures the binding strength between an antigenic determinant and an antibody-binding site. Avidity is the measure of the strength of binding between an antibody with its antigen. Avidity is related to both the affinity between an epitope with its antigen binding site on the antibody, and the valence of the antibody, which refers to the number of antigen binding sites of a particular epitope. The lesser the value of the $K_d$, the stronger the binding strength between an antigenic determinant and the antibody binding site.

The present invention also provides a polynucleotide that encodes a heavy chain of an antibody of the present invention (e.g., Antibody 1—SEQ ID NO: 13), or polynucleotides that comprise any one of the VH regions or a portion thereof, or any one of the VH CDRs, including any variants thereof, of an antibody of the present invention (e.g., Antibody 1). The present invention also provides a polynucleotide that encodes a light chain of an antibody of the present invention (e.g., Antibody 1—SEQ ID NO: 11), or polynucleotides that comprise any one of the VL regions or a portion thereof, or any one of the VH CDRs, including any variants thereof, of an antibody of the present invention (e.g., Antibody 1).

The invention also includes expression vectors comprising any of the polynucleotides described herein. Exemplary vectors include plasmids, phagemids, cosmids, viruses and phage nucleic acids or other nucleic acid molecules that are capable of replication in a prokaryotic or eukaryotic host such as a cell, e.g., a mammalian cell. Typical expression vectors contain transcription and translation terminators, initiation sequences, and promoters useful for regulation of the expression of the nucleic acid molecules of the invention. The vectors may also contain genetic expression cassettes containing an independent terminator sequence, sequences permitting replication of the vector in both eukaryotes and prokaryotes, i.e., shuttle vectors and selection markers for both prokaryotic and eukaryotic systems. The vectors typically contain a marker to provide a phenotypic trait for selection of transformed hosts such as conferring resistance to antibiotics such as ampicillin or neomycin.

Suitable promoters include constitutive promoters and inducible promoters. Representative expression control sequences/promoters include the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha mating factors, promoters derived from the human cytomegalovirus, metallothionine promoter, murine mammary tumor virus promoter, Rous sarcoma virus promoter, polyhedrin promoter and promoters derived from polyoma, adenovirus, retrovirus, and simian virus, e.g., the early and late promoters of SV40.

The invention also includes non-human hosts such as cells containing a polynucleotide or a vector of the invention. By "host" it is meant a non-human multicellular organism or a "host cell," which refers to a cell or population of cells into which a polynucleotide or vector of the invention is introduced. A host cell of the present invention may be a eukaryotic cell or cell line, such as a plant, animal, vertebrate, mammalian, rodent, mouse, primate, or human cell, or cell line. Suitable eukaryotic cells include yeast and other fungi, insect cells, plant cells, human cells, and animal cells, including mammalian cells, such as hybridoma lines, COS cells, NS0 cells and CHO cells. By "a population of host cells," it is meant a group of cultured cells into which a polynucleotide or vector of the present invention can be introduced and expressed. Any host cells which will support expression from a polynucleotide or vector of the invention is intended.

A host of the present invention may also be prokaryotic. Suitable prokaryotic hosts include, for example, *E. coli*, such as *E. coli* SG-936, *E. coli* HB101, *E. coli* W3110, *E. coli* X1776, *E. coli* X2282, *E. coli* DHI, and *E. coli* MRC1, *Pseudomonas, Bacillus*, such as *Bacillus subtilis*, and *Streptomyces*.

The invention also includes methods of producing an antibody of the present invention, which entails culturing a host cell expressing one or more polynucleotides encoding an antibody of the present invention, and recovering the antibody from the culture medium.

The antibodies of the present invention can be used as medicaments in human medicine, administered by a variety of routes. Most preferably, pharmaceutical compositions comprising the antibodies of the present invention are for parenteral administration. Such pharmaceutical compositions can be prepared by methods well known in the art (See, e.g., *Remington: The Science and Practice of Pharmacy,* 19$^{th}$ Vol II, Part 7, pages 1447-1676 ed. (1995), A. Gennaro et al., Mack Publishing Co.) and comprise an antibody as disclosed herein, and a pharmaceutically acceptable carrier, diluent, or excipient.

As used herein, the terms "inhibit" or "neutralize" with respect to a bioactivity of an antibody of the invention means the ability to substantially antagonize, prohibit, prevent, restrain, slow, disrupt, eliminate, stop, reduce or reverse a bioactivity of human VEGFR-3, including, but not limited to, a human VEGFR-3 bioactivity as measured in Example 4 or 5 herein.

As used herein, the terms "treat" and "treatment" refer to therapeutic treatment, wherein the object is to prevent or slow down (lessen) an undesired physiological change associated with a disease or disorder. Beneficial or desired clinical results include alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. "Treatment" can also mean prolonging survival as compared to expected survival if not receiving treatment. Those in need of treatment include those already with the disease or disorder as well as those prone to having the disease or disorder.

The compositions of the invention may include a "therapeutically effective amount" of an antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects.

Therapy may be "first-line", i.e., as an initial treatment in patients who have had no prior anti-cancer treatments, either alone or in combination with other treatments; or "second-line", as a treatment in patients who have had one prior anti-cancer treatment regimen, either alone or in combination with other treatments; or as "third-line", "fourth-line", etc. treatments, either alone or in combination with other treatments.

Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of tumor.

Cancers treated by the invention include primary tumors and secondary or metastatic tumors that have metastasized through the lymph system (including those metastasized from lung, breast, or prostate).

Cancers that may be treated include tumors that are not vascularized, or not yet substantially vascularized, as well as vascularized tumors. The cancers may be comprised of non-solid tumors (such as leukemias and lymphomas) or may be solid tumors.

Types of cancers to be treated with the antibodies of the invention include ovarian cancer, human erythroleukaemia, head and neck cancer, breast cancer, renal cell carcinoma, pancreatic cancer, lung cancer and colon cancer. Further, given the role of the VEGF-C/VEGFR-3 pathway in promoting lymphangiogenesis and given that, for most types of cancer, the first site of metastasis are lymph nodes, blocking the VEGF-C/VEGFR-3 pathway would be expected to inhibit lymph node metastases, e.g. from breast, pancreatic, gastric or colorectal cancer (Roberts et al., Cancer Res., 66(5), 2650-2657 (2006)).

The antibody may be administered alone (monotherapy), or in combination with one or more therapeutically effective agents or treatments (combination therapy). The other therapeutically effective agent may be conjugated to the antibody, incorporated into the same composition as the antibody, or may be administered as a separate composition. The other therapeutically effective agent or treatment may be administered prior to, during and/or after the administration of the antibody. The other therapeutically effective agent may be administered to augment the therapeutic effect of the antibody, or to diminish the negative side effects of the antibody.

The methods of treatment described herein can be used to treat any suitable mammal, including primates, such as monkeys and humans, horses, cows, cats, dogs, rabbits, and rodents such as rats and mice. In one embodiment, the mammal to be treated is human.

It will be seen by reference to the following examples that Antibody 1 binds an epitope on human VEGFR-3 comprising P219 as the dominant constituent of the epitope, V175 as a subordinate constituent of the epitope and L221 as a minor constituent of the epitope. Further it can be seen that Antibody 2 (a reference rat monoclonal antibody raised against murine VEGFR-3) binds an epitope on murine VEGFR-3 which comprises the residues L219 and V221. In addition, the examples also demonstrate that Antibody 1 has high affinity for human VEGFR-3 (56 pM), is able to block the binding of the ligand VEGF-C to VEGFR-3, is able to block the VEGF-C stimulated mitogenic response and is effective in in vivo xenograft models of ovarian cancer and HEL. Finally, it can also be seen that Antibody 2 is effective in xenograft models of head and neck cancer, breast cancer, lung cancer, RCC, pancreatic cancer and colon cancer.

EXAMPLE 1

The antibodies of the present invention may be made and purified using various suitable methods that are well known in the art. For example an appropriate host cell, such as HEK 293 EBNA or CHO, is either transiently or stably transfected with an expression system for secreting antibodies using an optimal predetermined light chain to heavy chain vector ratio or a single vector system encoding both a light chain (e.g. SEQ ID NO: 12 for Antibody 1) and a heavy chain (e.g. SEQ ID NO: 14 for Antibody 1). Clarified medium into which the antibody has been secreted is purified using any of many commonly-used techniques. For example, the medium may be conveniently applied to a Protein A or G Sepharose FF column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 2.5). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. or may be lyophilized. The CDR and variable region amino acid sequences (determined using the Kabat method) for Antibody 1 are provided below.

TABLE 1

Light Chain CDR Amino Acid Sequences

| mAb | LCDR1 | LCDR2 | LCDR3 |
|---|---|---|---|
| Antibody 1 | RASQSISSSFLA (SEQ ID NO: 1) | AASTRAT (SEQ ID NO: 2) | QQYGRSLS (SEQ ID NO: 3) |

TABLE 2

Heavy Chain CDR Amino Acid Sequences

| mAb | HCDR1 | HCDR2 | HCDR3 |
|---|---|---|---|
| Antibody 1 | GNSATWN (SEQ ID NO: 6) | RTYYRSKWNHDYAESVKS (SEQ ID NO: 7) | GDSSSWYAFDY (SEQ ID NO: 8) |

TABLE 3

LCVR, HCVR, Light chain & Heavy chain Amino Acid Sequences

| mAb | LCVR | HCVR | Light chain (signal sequence at residues 1-19) | Heavy chain (signal sequence at residues 1-19) |
|---|---|---|---|---|
| Antibody 1 | SEQ ID NO: 5 | SEQ ID NO: 10 | SEQ ID NO: 12 | SEQ ID NO: 14 |

EXAMPLE 2

In the following example, experiments are described which lead to the elucidation of the epitope on the VEGFR-3 receptor to which Antibody 1 and Antibody 2 bind.

Production of VEGF-$C_{\Delta N \Delta C}$ and mouse and human sR3-AP. Recombinant mature human VEGF-$C_{\Delta N \Delta C}$ is generated as described in Pytowski, et al., (2005) J. Natl. Cancer Inst. 97(1):14-21. The full-length (i.e., Ig domains 1-7) soluble extracellular regions of human and mouse VEGFR-3 (sR3) are fused to cDNA encoding human alkaline phosphatase (AP) to generate the fusion protein sR3-AP (Persaud et al., (2004) J. Cell Science 117:2745-56; Pytowski, et al. (2005) J. Natl. Cancer Inst. 97(1):14-21).

Production of mouse-human chimeric sR3-AP and site-directed mutants of sR3-AP. Chimeric mouse-human and human-mouse constructs of the 3 N-terminal immunoglobulin-like (Ig) domains of sR3-AP are prepared using overlapping PCR technique (Ho, et al., (1989), Gene 77:51-59) and are cloned into the AP expression vector (Persaud, et al., supra; Pytowski, et al., supra). Site-directed mutagenesis of sR3-AP constructs is performed using the QuickChange II XL Site-Directed Mutagenesis Kit per manufacturer's instructions (Stratagene). The presence of desired substitutions is verified by sequencing of both strands of the cDNA across the mutated region using the ABI Prism 3100 Genetic analyzer (Applied Biosystems) and the BigDye Terminator v3.1 Cycle Sequencing Kit (Applied Biosystems).

Expression of soluble VEGFR-3 proteins: The cDNA encoding extracellular regions of wild-type and mutated sR3-AP is transfected into FreeStyle™ 293 cells (Invitrogen, #R79007) cultured in suspension in a chemically-defined, protein-free FreeStyle™ 293 Expression Medium (Invitrogen, #12338026). In some cases, selected sR3-AP is purified using anti-AP antibody-affinity chromatography as previously described (Zhu, et al., (1998) Cancer Res. 58:3209-14) or by affinity chromatography with immobilized mAbs Antibody 1 and Antibody 2 described herein.

Normalization of sR3 proteins in conditioned medium (CM): CM is assayed for AP activity using the Great EscAPe™ SEAP Chemiluminescence kit 2.0 (Clontech, Mountain View, Calif.) using the Tropix TR7171 luminometer (Applied Biosystems, Foster City, Calif.). The CM is diluted in proportion to their AP activity in phosphate-buffered saline (PBS) containing 1% bovine serum albumin (PBS-BSA) and retested to verify the normalization by AP activity measurements and by Western blotting.

sR3-AP binding assays: One hundred (100) μl of normalized CM is transferred to 96-well microliter plates coated with either VEGF-$C_{\Delta N \Delta C}$, or the test antibody (200 ng/well). After 2 hr incubation, the plates are washed 5 times and bound sR3-AP is detected by chemiluminescence.

The binding specificity of Antibody 1 and a reference rat monoclonal antibody against mouse VEGFR-3 (designated 'Antibody 2') are tested by ELISA using the immobilized extracellular portions of mouse and human VEGFR-3 (Ig domains 1-7). Antibody 1 and Antibody 2 bind strongly and in a dose-dependent manner to human and mouse VEGFR-3 respectively. The human antibody Antibody 1 shows slight but reproducible cross-reactivity with mouse VEGFR-3 at concentrations exceeding 10 nM. In contrast, Antibody 2 fails to demonstrate any detectable binding to human VEGFR-3.

Epitopes of Antibody 1 and Antibody 2 are entirely contained within the second immunoglobulin-like (Ig) domain of VEGFR-3: The ligand-binding sites of all three members of VEGF receptor family are contained within the three N-terminal Ig domains of the extracellular domain. The species-specificity of Antibody 1 and Antibody 2 is utilized to ascertain which of the first three Ig domains contains the epitopes of these antibodies. DNA sequences encoding mouse and human Ig domains 1-3 are swapped in various combinations to form the following VEGFR-3 extracellular domain constructs: i) wild-type human; ii) wild-type mouse; iii) chimera 1 (human Ig1-human Ig2-mouse Ig3); chimera 2 (human Ig1-mouse Ig2-mouse Ig3); (iv) chimera 3 (mouse Ig1-human Ig2-mouse Ig3) and (v) chimera 4 (human Ig1-mouse Ig2-human Ig3). The constructs are expressed as fusion proteins with alkaline phosphatase (AP) Persaud, et al., supra. The encoded proteins are isolated from conditioned media (CM) of transiently transfected cells and normalized to equal protein concentration and AP activity. Mouse and human sR3-AP bind human VEGF-$C_{\Delta N \Delta C}$ with similar affinity. Thus, the ability of the various sR3-AP chimeras to bind human VEGF-$C_{\Delta N \Delta C}$ is tested as a means to determine that correct protein folding is preserved in the chimeric receptors. The ability of Antibody 1 and Antibody 2 to bind to chimeric proteins 1 to 4 show that the epitopes of Antibody 1 and Antibody 2 are completely contained within the second Ig domain (Ig2) of human and mouse VEGFR-3 respectively. For example, Antibody 1 will not bind to chimera 2 or chimera 4, which contain the mouse VEGFR3 sequence at Ig domain 2.

Identification of amino acids of VEGFR-3 that constitute the epitopes of Antibody 1 and Antibody 2: The twelve (12) positions within the amino acid sequence of the second Ig domain of VEGFR-3 that differ between the human and mouse proteins are identified. These positions along with the residues in the human and mouse proteins are shown in Table 4.

TABLE 4

| | Position | | | | | | | | | | |
|---|---|---|---|---|---|---|---|---|---|---|---|
| | 153 | 167 | 175 | 177 | 184 | 192 | 194 | 199 | 214 | 219 | 221 |
| Human | A | V | V | W | V | L | S | H | D | P | L |
| Mouse | S | I | A | H | L | R | P | R | N | L | V |

Site-directed mutagenesis is used to individually change each of the species-specific amino acids in the human and mouse sequence to the corresponding orthologue of the opposite species; each mutated protein is then expressed in the context of sR3-AP proteins encoding the first, second and third Ig domains. Epitope mapping is accomplished by two complementary approaches. In the first approach, the loss of binding of the human-specific Antibody 1 and the mouse-specific Antibody 2 to their respective human and mouse sR3-AP due to individual amino acid substitutions to the mouse or human orthologues is measured. In the second approach, the gain of binding of Antibody 1 and Antibody 2 to the sR3-AP of the opposite species mediated by individual amino acid substitutions to the mouse or human orthologues is measured. A residue is considered as a strong candidate to constitute a part of an epitope of an antibody if the mutations described above lead to loss of binding with the first approach and a gain of binding with the second approach. For all mutant proteins, the binding to VEGF-$C_{\Delta N \Delta C}$ is measured in parallel to check against gross changes in protein structure.

The binding experiments are carried out in triplicate and the results are calculated as the average and standard deviation of the three separate experiments. Of the 12 substitutions examined in the Ig2 domain of human sR3-AP, only one (V184L) leads to complete loss of binding to both VEGF-$C_{\Delta N \Delta C}$ and Antibody 1. This change is thus considered as disturbing the overall structure of the human sR3-AP. The substitution V175A leads to approximately 50% loss of binding to both VEGF-C and to Antibody 1. The substitution P219L results in approximately 75% loss in binding to VEGF-C and nearly complete (~95%) loss of binding to Antibody 1. Change of L221 to V does not affect binding of human sR3-AP to VEGF-C but reduces binding to Antibody 1 by about 55%. The remaining substitutions do not lead to a substantial loss of binding to either VEGF-C or Antibody 1.

When individual mouse to human mutations in the mouse sR3-AP are examined for increased binding to the human specific Antibody 1, a significant increase above binding to wild-type mouse sR3-AP is observed for the substitutions A175V (~12-fold) and L219P (~60-fold). None of the other substitutions lead to a significant increase of binding above background.

The criteria are thus set for considering an amino acid to comprise an epitope for Antibody 1 wherein human to mouse orthologue substitution in human sR3-AP would significantly reduce binding to Antibody 1 while reducing (but NOT abolishing) or leaving unaffected the binding to VEGF-$C_{\Delta N \Delta C}$. In addition, for an amino acid to comprise an epitope for Antibody 1, mouse to human orthologue substitution in mouse sR3-AP would lead to significant binding to Antibody 1. For Antibody 1, these criteria are satisfied by V175 and P219 of human sR3-AP. V184 is excluded because a substitution in human sR3-AP to the mouse orthologue abolishes both binding to VEGF-$C_{\Delta N \Delta C}$ and to Antibody 1 while the corresponding substitution in mouse sR3-AP to the human orthologue at this position does not lead to binding to Antibody 1. Changing leucine 221 in human sR3-AP to the corresponding murine valine reduces binding to Antibody 1 by 55%. However, the corresponding substitution in mouse sR3-AP to the human orthologue at this position does not lead to binding to Antibody 1. Therefore L221 may make a minor contribution to the epitope of Antibody 1 but does not meet all the criteria established above.

To study the role of the residue at position 221 further, the P219L and L221V mutations in human sR3-AP are combined into a single construct. The binding of the double mutant to Antibody 1 is essentially abolished as compared to the single P219L mutant that retains 5% of binding to human sR3-AP.

Taken together, these results identify P219 as the dominant and V175 as a subordinate constituent of the epitope of Antibody 1 on human VEGFR-3 and raise the possibility that L221 is also a minor component of the epitope.

An examination is then made as to which residues of Ig domain 2 of the mouse VEGFR-3 constitute the epitope of Antibody 2 using a similar method. Again, the binding experiments are carried out in triplicate and the results are calculated as the average and standard deviation of the three separate experiments. Of the twelve individual substitutions that change the mouse amino acid into the corresponding human amino acid, four substitutions (H177W, P194S, R199H and N214D) significantly reduce binding of mouse sR3-AP to both VEGF-C and Antibody 2. Interestingly, mutations at positions 219 and 221 (L219P and V221L) reduce binding to Antibody 2 but not to VEGF-C. The corresponding human to mouse mutations in human VEGFR-3 at positions 219 and 221 (P219L and L221V) permit the binding of Antibody 2 to the human sR3-AP at levels, respectively approximately 55-fold and 10-fold, greater than the binding of Antibody 2 to the wild type human sequence. It is also demonstrated that the binding of the mouse mutant proteins containing the human orthologue amino acid at positions 219 and 221 to VEGF-$C_{\Delta N \Delta C}$ increases slightly or is unaffected while the binding of these mutant proteins to Antibody 2 is either abolished (219) or reduced by about 85% (221).

The criteria set for considering an amino acid to comprise an epitope for Antibody 2 is that human orthologue substitution in mouse sR3-AP would significantly reduce binding to Antibody 2 while reducing (but NOT abolishing) or leaving unaffected the binding to VEGF-$C_{\Delta N \Delta C}$. In addition, for an amino acid to comprise an epitope for Antibody 2, human to mouse orthologue substitution in human sR3-AP would lead to significant binding to Antibody 2. For Antibody 2, these criteria are satisfied by P219 and L221 of the mouse sR3-AP.

Another method to express the data is to calculate the percentage of maximal binding of Antibody 2 to wild type mouse sR3-AP that is reconstituted by each of the individual human to mouse orthologue mutations within the human sR3-AP sequence. This demonstrates that individually substituting P219L and L221V within the sequence of human sR3-AP results in the reconstitution of about 5% and 1% respectively of the maximal binding to Antibody 2 seen with wild type mouse sR3-AP. It is therefore concluded that L219 and V221 are constituents of the epitope of Antibody 2.

It can be seen that Antibody 1 and Antibody 2 bind highly similar epitopes in human VEGFR-3 and mouse VEGFR-3 respectively, with the residue at position 219 being the key residue in each case. The data in the following examples demonstrate that both Antibody 1 and Antibody 2 are neutralising antibodies which are able to block the activity of their respective antigens as well as inhibit tumour growth in in vivo xenograft models. Such data provides further evidence to demonstrate that the novel epitope in the Ig2 domain of VEGFR-3 identified herein provides the key advantageous feature of being a neutralising epitope. Antibodies binding to said epitope are thus able to block ligand binding, VEGFR-3 signalling and inhibit tumour growth in vivo.

EXAMPLE 3

Affinity ($K_d$) Measurements for Anti-VEGFR-3 Antibodies

The binding kinetics of the Antibody 1 are measured by surface plasmon resonance on the BIACORE® 2000 biosensor (BIACORE®, Piscataway, N.Y.) at 20° C. Soluble extracellular domain of human VEGFR-3 (sR3-AP) is immobilized on a sensor chip and Antibody 1 is injected over the surface of the sensor at concentrations between 0.8 and 6.25 nM. Sensograms are evaluated using the BIA Evaluation 3.2 program to determine the on rates (ka) and the off rates (kd). The dissociation constant ($K_d$) is calculated from the ka and kd rates using the equation: $K_d$=ka/kd. BIAcore kinetic analysis yields a $K_d$ of 56 pM for the binding of Antibody 1 to immobilized sR3-AP. Thus, Antibody 1 has an extremely high affinity for human VEGFR-3 wherein said affinity is nearly 2 orders of magnitude greater than that of sR3-AP for VEGF-$C_{\Delta N \Delta C}$.

EXAMPLE 4

Blockade of VEGF-C Binding to VEGFR-3 by anti-VEGFR-3 Antibodies

To measure the ability of VEGFR-3 antibodies to block VEGF-C binding to human VEGFR-3, a competitive VEGF-C blocking assay is utilized. Antibodies or soluble phage particles at a concentration of 0.001 µg/ml to 5 µg/ml are mixed with 50 ng of sR3-AP, incubated at room temperature for 1 hour and transferred to 96-well microtiter plates coated with VEGF-$C_{\Delta N \Delta C}$ (200 ng/well). After an additional 2 hours, the plates are washed five times and p-nitrophenyl phosphate (Sigma) is added to quantify the bound sR3-AP molecules at $OD_{405nm}$. The $IC_{50}$, i.e. the concentration of Fab or IgG required for 50% inhibition of sR3-AP binding to VEGF-$C_{\Delta N \Delta C}$, is calculated. The Fab and IgG forms of Antibody 1 strongly block the binding of sR3-AP to immobilized VEGF-$C_{\Delta N \Delta C}$ with an $IC_{50}$ of 2 and 1.3 nM, respectively. By contrast, a control antibody which targets the human IGF receptor and is obtained from the same phage library is inactive.

EXAMPLE 5

Inhibition of VEGF-$C_{\Delta N \Delta C}$-stimulated Mitogenic Response by Antibody 1

In order to test the ability of Antibody 1 to inhibit signal transduction mediated by VEGFR-3, a NIH-3T3 cell line is prepared that expresses a chimeric form of VEGFR-3 which fuses the extracellular domain of human VEGFR-3 with the transmembrane and cytoplasmic domains of human cFMS. No endogenous expression of VEGFR-3 by the parental cells is detected, and localization of the chimeric receptor on the plasma membrane is shown by FACS analysis. VEGFR-3-FMS cells ($5 \times 10^3$ cells/well) are plated onto 96-well tissue culture plates (Wallac, Gaithersburg, Md.) in 200 ml of serum free medium and incubated at 37° C. for 72 hours. Antibody up to 20 nM is added and pre-incubated at 37° C. for 1 hour, after which VEGF-$C_{\Delta N \Delta C}$ is added to a final concentration of 20 ng/ml. After 18 hours of incubation, 0.25 mCi of tritiated thymidine ([$^3$H]-TdR) (Amersham) is added to each well and incubated for an additional 4 hours. The cells are placed on ice, washed once with serum containing medium, incubated for 10 minutes at 4° C. with 10% TCA, and solubilized in 25 ml of 2% SDS. Incorporated radioactivity is determined on a scintillation counter (Wallac, Model 1450 Microbeta Scintillation Counter). The incorporation of [$^3$H]-TdR by the NIH-3T3 cells that express VEGFR-3-cFMS is stimulated by at least threefold by the addition of VEGF-$C_{\Delta N \Delta C}$. The mitogenic response is specifically blocked in a dose-dependent manner by Antibody 1, with an $IC_{50}$ value of 5 nM.

EXAMPLE 6

Anti-VEGFR-3 Monoclonal Antibodies in a Human Ovarian Carcinoma Cell Line Subcutaneous Xenograft Model In this experiment, anti-VEGFR3 monoclonal antibodies Antibody 1 and Antibody 2 are used alone or in combination on xenografts of human ovarian carcinoma cell line OVCAR-8 (NCl-60, Developmental Therapeutics Program, NCI/NIH) in immunodeficient SCID mice. OVCAR-8 is one of very few human carcinoma cell lines that express human VEGFR-3. The expectation in this experiment is that Antibody 2 will block angiogenesis and lymphangiogenesis in the mouse stroma of the growing tumor while having no effect on the tumor. In contrast, Antibody 1 is expected to only act on the human carcinoma cells.

OVCAR-8 cells are injected s.c. into the left flank of 75 female athymic mice at $1 \times 10^7$ cells/mouse. When tumors reach ~180 mm$^3$, 13 days after cell implantation, the mice are randomized and divided into five treatment groups (n=12): USP saline control, 0.5 ml/dose; Rat IgG at 40 mg/kg; Antibody 1 at 40 mg/kg; Antibody 2 at 40 mg/kg and Antibody 1 at 40 mg/kg+Antibody 2 at 40 mg/kg. Anti-VEGFR-3 mAbs and controls are given i.p. on a Mon-Wed-Fri schedule. Tumor measurements are recorded twice weekly. The T/C % is calculated for each treatment group as the ratio of the relative tumor volume of each treatment group versus the relative tumor volume of the saline control group. RM ANOVA through Day 41 is used to compare tumor growth among the treatment groups.

Antibody 2 significantly inhibits the growth of OVCAR-8 tumors with a T/C % of 71% (P=0.0299). Antibody 1 has a trend toward efficacy in this model (T/C % was 74%) but the degree of tumor inhibition does not reach significance (P>0.05). This may be due to the wide range of tumor volumes at Day 41 in this group (335-1504 mm$^3$) that may have prevented this group from reaching statistical significance.

The combination of Antibody 1 and Antibody 2 together enhances the tumor inhibitory effect of Antibody 2 (T/C % was 47% and the combination effect reaches significance compared to either antibody alone (P≦0.0358)).

Antibody 2 significantly inhibits the growth of OVCAR-8 tumors while Antibody 1 appears to be efficacious in this model without reaching statistical significance. However, since the combination of the two monoclonal antibodies significantly inhibits OVCAR-8 tumor growth compared to Antibody 2 monotherapy, it is concluded that Antibody 1 demonstrated therapeutic efficacy in this experiment. Accordingly, the antibodies of the present invention demonstrate anti-tumour efficacy in an in vivo model of ovarian cancer.

EXAMPLE 7

Anti-VEGFR-3 mAb Antibody 1 in the Human Erythroleukemia (HEL) Cell Subcutaneous Xenograft Model In the following example, a significant anti-tumor effect is measured for Antibody 1 in the human erythroleukemic (HEL) cell subcutaneous xenograft model.

Nu/nu mice (female, 7-8 weeks) housed 5-6 per cage are injected subcutaneously with $5 \times 10^6$ HEL cells/mouse. When tumors reach approximately 400 mm³, mice are randomized by tumor volume into one of four treatment groups (n=11/group):
1) USP saline, 10 ml/kg,
2) Antibody 1, 60 mg/kg (loading dose of 150 mg/kg on Day 1)
3) Antibody 1, 20 mg/kg (loading dose of 50 mg/kg on Day 1)
4) Antibody 1, 6 mg/kg (loading dose of 15 mg/kg on Day 1)

Antibody 1 is prepared in USP saline. Treatments are administered i.p., twice a week, at 10 ml dosing solution/kg of body weight. The first dose, the loading dose, is administered on Day 1, followed by the maintenance dose administered twice a week for the duration of the study. Tumor volumes are measured twice a week. Body weights are recorded at least twice a week for the duration of the study. The T/C % is calculated for each treatment group on Day 18 as the ratio of the relative tumor volume of each treatment group versus the relative tumor volume of the saline control group (Table 5). Tumor growth and body weight change in the treatment groups are compared by Repeated Measures ANOVA.

Treatment with Antibody 1 results in a dose dependent inhibition of HEL tumor growth, with 60 mg/kg Antibody 1 significantly inhibiting tumor growth (p=0.0031). There is no effect on body weight with Antibody 1 treatment in this study (Table 5). Accordingly, the antibodies of the present invention demonstrate anti-tumor efficacy in an in vivo model of HEL, while resulting in minimal adverse side effects in that model.

TABLE 5

|  | T/C% on Day 18 | RM ANOVA for Tumor Volume | Final Mean % Body Weight Change | RM ANOVA for Body Weight |
|---|---|---|---|---|
| Saline Control |  |  | 6.6 |  |
| Antibody 1 60 mg/kg | 52.5 | 0.0031 | 4.6 | 0.21 |
| Antibody 1 20 mg/kg | 69.6 | 0.13 | 3.2 | 0.20 |
| Antibody 1 6 mg/kg | 81.9 | 0.39 | 4.6 | 0.41 |

EXAMPLE 8

Anti-VEGFR-3 mAb Antibody 2 in Combination with Cisplatin in the CAL27 Squamous Cell Carcinoma Xenograft Model In order to test for activity of anti-VEGFR-3 antibodies in head and neck cancer, the CAL27 xenograft model is used. CAL27 cell suspension, at $1\times10^7$ cells/mouse, is injected s.c. into the left flank of 60 female athymic mice. When tumors reach ~180 mm³, eight days after cell implantation, the mice are randomized and divided into four treatment groups (n=12): 1.) USP saline control, 0.5 ml i.p., 3 days per week 2.) Antibody 2 at 40 mg/kg, 3 days per week 3.) cisplatin at 7 mg/kg, q7d 4.) Antibody 2 at 40 mg/kg, 3 days per week+cisplatin at 7 mg/kg, q7d.

Tumor measurements are recorded twice weekly; RM ANOVA through Day 61 is used to compare tumor growth among the treatment groups. Chi Squared tests are used to test for statistical significance in the number of tumor regressions among the treatment groups.

Monotherapy using Antibody 2 or cisplatin significantly inhibits the growth of CAL27 tumors compared to the USP saline control (P≦0.0077). The T/C % values are 55% and 39% for Antibody 2 and for cisplatin, respectively. Combination therapy with both Antibody 2 and cisplatin results in significant inhibition of tumor growth when compared to monotherapy (P≦0.0322). The effect of combination therapy is greater-than-additive as determined by the Fractional Product Method. Accordingly, an anti-VEGFR-3 antibody binding to an epitope in the Ig2 domain of VEGFR-3 demonstrates anti-tumor efficacy in an in vivo model of head and neck cancer either as a monotherapy or in combination with cisplatin.

EXAMPLE 9

Anti-VEGFR-3 mAb Antibody 2 in Combination with 5-Fluorouracil/Leucovorin in an MDA-MB-231 Breast Cancer Xenograft Model In order to test for activity of anti-VEGFR-3 antibodies in breast cancer, the MDA-MB-231 xenograft model is used. NIH nu/nu athymic mice (female 8 weeks) are injected subcutaneously in the mammary fat pad with $6\times10^6$ MDA-MB-231 cells in 0.4 ml (1:1 w/matrigel). When tumors reach approximately 300 mm³, mice are randomized by tumor size into the following treatment groups (n=12): 1) USP saline 10 µl/g, 3 times per week 2) 40 mg/kg Antibody 2, 3 times per week 3) 125 mg/kg 5FU (5-Fluorouracil)+62 mg/kg LV (Leucovorin), once per week 4) Antibody 2 at 40 mg/kg, 3 times per week+5FU/LV at 125 mg/kg and 62 mg/kg, respectively, once per week. All agents are prepared the day of treatment and administered i.p. Cytotoxic treatment is started one day prior to the start of antibody treatment.

A comparison of the tumor volumes from the saline control group versus the tumor volumes of the treated mice shows significant tumor growth inhibition with Antibody 2 or Antibody 2+5FU/LV administration (see Table 6). While the effects of the combination of Antibody 2+5-FU/LV are not greater than that of the monotherapies, there is a trend for increased antitumor effects for the combination. Accordingly, an anti-VEGFR-3 antibody binding to an epitope in the Ig2 domain of VEGFR-3 demonstrates anti-tumor efficacy in an in vivo model of breast cancer (compared to saline control) either as a monotherapy or in combination with 5FU/LV.

TABLE 6

|  | Tumor Volumes | |
|---|---|---|
|  | [1]p- value | T/C % |
| Antibody 2 v. USP saline | p = 0.04 | 49 |
| 5FU/LV v. USP saline | p = 0.17 | 52 |
| Antibody 2 + 5FU/LV v. USP saline | p < 0.01 | 28 |
| Antibody 2 v. Antibody 2 + 5FU/LV | p = 0.09 | 57 |
| 5FU/LV v. Antibody 2 + 5FU/LV | p = 0.09 | 54 |

[1]RM ANOVA through Day 34

EXAMPLE 10

Anti-VEGFR-3 mAb Antibody 2 alone and in Combination with Docetaxel in a NCI-H292 Lung Cancer Xenograft Model In order to test for activity of anti-VEGFR-3 antibodies in lung cancer, the NCI-H292 xenograft model is used. Nu/nu mice (female, 7-8 weeks of age) are injected subcutaneously with $2\times10^6$ NCI-H292 cells/mouse. When tumors reach approximately 300 mm³, mice are randomized by tumor size into the following treatment groups (n=15): 1) USP saline at 10 μl/g, 3 times per week, i.p., starting on day 2. 2) Antibody 2 at 40 mg/kg, 3 times per week, i.p., starting day 2. 3) Docetaxel at 12 mg/kg, q7d, starting day 1. 4) Docetaxel at 12 mg/kg, q7d, starting day 1 plus Antibody 2 at 40 mg/kg, 3 times per week, starting day 2.

Tumor volumes are measured approximately twice a week and body weights are recorded at least twice a week for the duration of the study. At sacrifice, mice are euthanized by $CO_2$ asphyxiation. The T/C % is calculated for each treatment group as the ratio of the relative tumor volume in the experimental groups versus the control group. Tumor growth and body weights are compared to the control group by repeated measures ANOVA through Day 26.

Treatment with Antibody 2 and Docetaxel significantly inhibits NCI-H292 tumor growth with T/C % values of 74% and 49%, respectively. Combination therapy of Antibody 2 and Docetaxel significantly increases antitumor efficacy compared to either monotherapy with a T/C % of 24%. Accordingly, an anti-VEGFR-3 antibody binding to an epitope in the Ig2 domain of VEGFR-3 demonstrates anti-tumor efficacy in a further in vivo model of lung cancer either as a monotherapy (p=<0.0001) or in combination with Docetaxel (p=<0.0001).

EXAMPLE 11

Anti-VEGFR-3 mAb Antibody 2 in a Subcutaneous SK-RC-29 Human Renal Cell Carcinoma (RCC) Xenograft Model In order to test for activity of anti-VEGFR-3 antibodies in RCC, the SK-RC-29 Human Renal Cell Carcinoma xenograft model is used. Female athymic nu/nu mice (n=12 per group) are implanted s.c. with $2 \times 10^6$ SK-RC-29 RCC cells per mouse. The cells are injected as a mixture in 1:1 Matrigel® basement membrane (Vt=0.4 ml). When tumors reach 200-250 mm³, mice are randomized into groups and i.p. dosing is initiated with control group receiving USP Saline (500 μl/injection) and Antibody 2 group receiving 60 mg/kg for the first dose and 40 mg/kg on all subsequent doses. Tumor volume measurements are recorded twice weekly, for 43 days. Representative tumor samples (n=4 per treatment group) were taken at day 48 (end of the study) for histological analysis. To determine the significance of anti-tumor effects between treatment groups, statistical analysis was performed using Repeated Measures (RM) ANOVA. Weight loss due to antibody toxicity did not occur in any of the treatment groups as measured day 47. In fact, the weight of the mice treated with antibody increased by approximately 5.5% over the course of the study.

To assess anti-tumor efficacy and calculate T/C % values, all treatment groups are compared to control mice up to day 32. Antibody 2 yields a T/C % of 62% (p=0.012); this demonstrates inhibition of the growth of renal cell carcinoma in a subcutaneous xenograft model with minimal adverse side effects.

EXAMPLE 12

Anti-VEGFR-3 mAb Antibody 2 in BxPC-3 Pancreatic Carcinoma Xenografts

In order to test for activity of anti-VEGFR-3 antibodies in pancreatic carcinoma, the BxPC-3 Pancreatic Carcinoma Xenograft model is used. Female athymic nu/nu mice (n=36) are injected s.c. with $2 \times 10^6$ BxPC-3 human pancreatic cells/mouse mixed in 1:1 Matrigel. When tumors reach ~350 mm³, the animals are separated into three treatment groups (n=10): 1) USP saline. 2) mAb Antibody 2 at 10 mg/kg. 3) mAb Antibody 2 at 40 mg/kg. All treatments are administered i.p. three times per week at 0.1 ml/10 g body weight. Tumor volume measurements are recorded twice weekly, for six weeks.

Antibody 2 treatment inhibits growth of BxPC-3 tumors in a dose-dependent manner. At the end of the study on Day 40, the T/C values are 75% (p=0.042) and 56% (p=0.002) for the 10 mg/kg and 40 mg/kg dose groups, respectively.

EXAMPLE 13

Anti-VEGFR-3 mAb Antibody 2 in Combination with Oxaliplatin on HT-29 Colon Xenografts In order to test for activity of anti-VEGFR-3 antibodies in colon cancer, the HT-29 Colon xenograft model is used. HT-29 cell suspension, at $5 \times 10^6$/mouse, is injected s.c. into the left flank of 60 female athymic mice. When tumors reach ~180 mm³, eight days after cell implantation, the mice are randomized and divided into four treatment groups (n=12): 1) USP saline control, 0.5 ml i.p., three times per week. 2) Antibody 2 at 40 mg/kg, three times per week. 3) oxaliplatin at 12 mg/kg, q7d. 4) Antibody 2 at 40 mg/kg, three times per week+oxaliplatin at 12 mg/kg, q7d.

Tumor measurements are recorded twice weekly; RM ANOVA is used to compare tumor growth among the treatment groups. Antibody 2 alone does not significantly inhibit the growth of HT-29 tumors; the antibody has a trend for efficacy with a T/C % of 80%. Combination therapy with both Antibody 2 and oxaliplatin significantly inhibits the growth of HT-29 tumors compared to control or to either monotherapy (P≦0.0280) with a T/C % of 47%. Accordingly, an anti-VEGFR-3 antibody binding to an epitope in the Ig2 domain of VEGFR-3 demonstrates anti-tumor efficacy in an in vivo model of colon cancer when used in combination with oxaliplatin.

---

We claim:

1. An antibody or fragment thereof that binds to human VEGFR-3 comprising a LCDR1 of SEQ ID NO: 1, a LCDR2 of SEQ ID NO: 2, a LCDR3 of SEQ ID NO: 3, a HCDR1 of SEQ ID NO:6, a HCDR2 of SEQ ID NO: 7 and a HCDR3 of SEQ ID NO: 8.

2. The antibody or fragment thereof of claim 1, comprising a light chain variable region of SEQ ID NO: 5 and a heavy chain variable region of SEQ ID NO: 10.

3. The antibody or fragment thereof of claim 2, wherein the antibody comprises a light chain of SEQ ID NO: 15 and a heavy chain of SEQ ID NO: 16.

4. The antibody or fragment thereof of claim 3, wherein the antibody comprises two light chains of SEQ ID NO: 15 and two heavy chains of SEQ ID NO: 16.

5. A pharmaceutical composition comprising the antibody or fragment thereof of claim 4 together with a pharmaceutically acceptable carrier, diluent or excipient.

6. A pharmaceutical composition of claim 5 comprising an additional pharmaceutical agent, wherein the agent is cisplatin, 5-fluorouracil, leucovorin, oxaliplatin or docetaxel.

* * * * *

UNITED STATES PATENT AND TRADEMARK OFFICE
CERTIFICATE OF CORRECTION

PATENT NO. : 8,481,034 B2  
APPLICATION NO. : 13/223344  
DATED : July 9, 2013  
INVENTOR(S) : Bronislaw Pytowski Page 1 of 1

It is certified that error appears in the above-identified patent and that said Letters Patent is hereby corrected as shown below:

Title Page, Column 1, Line 3 (Other Publications), after "monoclonal" insert -- antibody --.

Signed and Sealed this  
Fifteenth Day of October, 2013

Teresa Stanek Rea  
*Deputy Director of the United States Patent and Trademark Office*

SEQUENCE LISTING

<160> NUMBER OF SEQ ID NOS: 22

<210> SEQ ID NO 1
<211> LENGTH: 12
<212> TYPE: PRT
<213> ORGANISM: Homo sapiens

<400> SEQUENCE: 1

Arg Ala Ser Gln Ser Ile Ser Ser Ser Phe Leu Ala
1               5                   10

-continued

```
<210> SEQ ID NO 2
<211> LENGTH: 7
<212> TYPE: PRT
<213> ORGANISM: Homo sapiens

<400> SEQUENCE: 2

Ala Ala Ser Thr Arg Ala Thr
1               5

<210> SEQ ID NO 3
<211> LENGTH: 8
<212> TYPE: PRT
<213> ORGANISM: Homo sapiens

<400> SEQUENCE: 3

Gln Gln Tyr Gly Arg Ser Leu Ser
1               5

<210> SEQ ID NO 4
<211> LENGTH: 321
<212> TYPE: DNA
<213> ORGANISM: Homo sapiens

<400> SEQUENCE: 4
gaaattgtgt tgacgcagtc tccaggcacc ctgtctttgt ctctagggga aagagccacc      60
ctctcctgca gggccagtca gagtattagc agcagcttct tagcctggta ccagcagaaa     120
cctggccagg ctcccaagct cctcatctat gctgcatcca ccagggccac tggcatccca     180
gacaggttca gtggcagtgg gtctgggaca gacttcactc tcaccatcag cagactggag     240
cctgaagatt ttgctgtcta ttactgtcag cagtatggtc gctcactctc tttcggcgga     300
gggaccaagg tggaggtcaa a                                                321

<210> SEQ ID NO 5
<211> LENGTH: 107
<212> TYPE: PRT
<213> ORGANISM: Homo sapiens

<400> SEQUENCE: 5

Glu Ile Val Leu Thr Gln Ser Pro Gly Thr Leu Ser Leu Ser Leu Gly
1               5                   10                  15

Glu Arg Ala Thr Leu Ser Cys Arg Ala Ser Gln Ser Ile Ser Ser Ser
            20                  25                  30

Phe Leu Ala Trp Tyr Gln Gln Lys Pro Gly Gln Ala Pro Lys Leu Leu
        35                  40                  45

Ile Tyr Ala Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Leu
                85                  90                  95

Ser Phe Gly Gly Gly Thr Lys Val Glu Val Lys
            100                 105

<210> SEQ ID NO 6
<211> LENGTH: 7
<212> TYPE: PRT
<213> ORGANISM: Homo sapiens

<400> SEQUENCE: 6

Gly Asn Ser Ala Thr Trp Asn
1               5
```

<210> SEQ ID NO 7
<211> LENGTH: 18
<212> TYPE: PRT
<213> ORGANISM: Homo sapiens

<400> SEQUENCE: 7

Arg Thr Tyr Tyr Arg Ser Lys Trp Asn His Asp Tyr Ala Glu Ser Val
1               5                   10                  15

Lys Ser

<210> SEQ ID NO 8
<211> LENGTH: 11
<212> TYPE: PRT
<213> ORGANISM: Homo sapiens

<400> SEQUENCE: 8

Gly Asp Ser Ser Ser Trp Tyr Ala Phe Asp Tyr
1               5                   10

<210> SEQ ID NO 9
<211> LENGTH: 369
<212> TYPE: DNA
<213> ORGANISM: Homo sapiens

<400> SEQUENCE: 9
caggtacagc tgcagcagtc aggtccagga ctggtgaagc cctcgcagac tctctcactc        60
acctgtgcca tctccgggga cagtgtctct ggcaacagtg ctacttggaa ctggatcagg       120
cagtccccat cgcgaggcct tgagtggctg ggaaggacat attacaggtc caagtggaat       180
catgattatg cagaatctgt gaaaagtcga ataaccatca cccagacac atccaagaac        240 cagttctccc tgcagctgaa ctctgtgact cccgaggaca cggctgtgta ttactgtgca       300
aggggtgata gcagcagctg gtacgccttt gactactggg gccagggcac cctggtcacc       360
gtctcaagc                                                               369

<210> SEQ ID NO 10
<211> LENGTH: 123
<212> TYPE: PRT
<213> ORGANISM: Homo sapiens

<400> SEQUENCE: 10

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Gly Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Asn His Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Asp Ser Ser Ser Trp Tyr Ala Phe Asp Tyr
            100                 105                 110

Trp Gly Gln Gly Thr Leu Val Thr Val Ser Ser
        115                 120

```
<210> SEQ ID NO 11
<211> LENGTH: 702
<212> TYPE: DNA
<213> ORGANISM: Homo sapiens

<400> SEQUENCE: 11
atgggatggt catgtatcat ccttttttcta gtagcaactg caactggagt acattcagaa      60
attgtgttga cgcagtctcc aggcaccctg tctttgtctc taggggaaag agccaccctc     120
tcctgcaggg ccagtcagag tattagcagc agcttcttag cctggtacca gcagaaacct     180
ggccaggctc ccaagctcct catctatgct gcatccacca gggccactgg catcccagac     240
aggttcagtg gcagtgggtc tgggacagac ttcactctca ccatcagcag actggagcct     300
gaagattttg ctgtctatta ctgtcagcag tatggtcgct cactctcttt cggcggaggg     360
accaaggtgg aggtcaaacg aactgtggct gcaccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                        702

<210> SEQ ID NO 12
<211> LENGTH: 233
<212> TYPE: PRT
<213> ORGANISM: Homo sapiens

<400> SEQUENCE: 12

Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
            20                  25                  30

Ser Leu Gly Glu Arg Ala Thr Leu Ser Cys Arg Ala Ser Gln Ser Ile
        35                  40                  45

Ser Ser Ser Phe Leu Ala Trp Tyr Gln Gln Lys Pro Gly Gln Ala Pro
    50                  55                  60

Lys Leu Leu Ile Tyr Ala Ala Ser Thr Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Gly
            100                 105                 110

Arg Ser Leu Ser Phe Gly Gly Gly Thr Lys Val Glu Val Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205
```

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 13
<211> LENGTH: 1419
<212> TYPE: DNA
<213> ORGANISM: Homo sapiens

<400> SEQUENCE: 13

| | | | | | |
|---|---|---|---|---|---|
| atgggatggt | catgtatcat | ccttttcta | gtagcaactg | caactggagt | acattcacag | 60 |
| gtacagctgc | agcagtcagg | tccaggactg | gtgaagccct | cgcagactct | ctcactcacc | 120 |
| tgtgccatct | ccggggacag | tgtctctggc | aacagtgcta | cttggaactg | gatcaggcag | 180 |
| tccccatcgc | gaggccttga | gtggctggga | aggacatatt | acaggtccaa | gtggaatcat | 240 |
| gattatgcag | aatctgtgaa | aagtcgaata | accatcaacc | cagacacatc | caagaaccag | 300 |
| ttctccctgc | agctgaactc | tgtgactccc | gaggacacgg | ctgtgtatta | ctgtgcaagg | 360 |
| ggtgatagca | gcagctggta | cgcctttgac | tactggggcc | agggcaccct | ggtcaccgtc | 420 |
| tcaagcgcta | gcaccaaggg | cccatcggtc | ttccccctgg | cacctcctc | caagagcacc | 480 |
| tctgggggca | cagcggccct | gggctgcctg | gtcaaggact | acttccccga | accggtgacg | 540 |
| gtgtcgtgga | actcaggcgc | cctgaccagc | ggcgtgcaca | ccttcccggc | tgtcctacag | 600 |
| tcctcaggac | tctactccct | cagcagcgtg | gtgaccgtgc | cctccagcag | cttgggcacc | 660 |
| cagacctaca | tctgcaacgt | gaatcacaag | cccagcaaca | ccaaggtgga | caagagagtt | 720 |
| gagcccaaat | cttgtgacaa | aactcacaca | tgcccaccgt | gcccagcacc | tgaactcctg | 780 |
| gggggaccgt | cagtcttcct | cttccccca | aaacccaagg | acaccctcat | gatctcccgg | 840 |
| accectgagg | tcacatgcgt | ggtggtggac | gtgagccacg | aagaccctga | ggtcaagttc | 900 |
| aactggtatg | tggacggcgt | ggaggtgcat | aatgccaaga | caaagccgcg | ggaggagcag | 960 |
| tacaacagca | cgtaccgtgt | ggtcagcgtc | ctcaccgtcc | tgcaccaaga | ctggctgaat | 1020 |
| ggcaaggagt | acaagtgcaa | ggtctccaac | aaagccctcc | cagcccccat | cgagaaaacc | 1080 |
| atctccaaag | ccaaagggca | gccccgagaa | ccacaggtgt | acaccctgcc | cccatcccgg | 1140 |
| gaggagatga | ccaagaacca | gtcagcctg | acctgcctgg | tcaaaggctt | ctatcccagc | 1200 |
| gacatcgccg | tggagtggga | gagcaatggg | cagccggaga | acaactacaa | gaccacgcct | 1260 |
| cccgtgctgg | actccgacgg | ctccttcttc | ctctattcca | agctcaccgt | ggacaagagc | 1320 |
| aggtggcagc | aggggaacgt | cttctcatgc | tccgtgatgc | atgaggctct | gcacaaccac | 1380 |
| tacacgcaga | agagcctctc | cctgtctccg | ggcaaatga | | | 1419 |

<210> SEQ ID NO 14
<211> LENGTH: 472
<212> TYPE: PRT
<213> ORGANISM: Homo sapiens

<400> SEQUENCE: 14

Met Gly Trp Ser Cys Ile Ile Leu Phe Leu Val Ala Thr Ala Thr Gly
1               5                   10                  15

Val His Ser Gln Val Gln Leu Gln Gln Ser Gly Pro Gly Leu Val Lys
            20                  25                  30

-continued

```
Pro Ser Gln Thr Leu Ser Leu Thr Cys Ala Ile Ser Gly Asp Ser Val
         35                  40                  45

Ser Gly Asn Ser Ala Thr Trp Asn Trp Ile Arg Gln Ser Pro Ser Arg
 50                  55                  60

Gly Leu Glu Trp Leu Gly Arg Thr Tyr Tyr Arg Ser Lys Trp Asn His
 65                  70                  75                  80

Asp Tyr Ala Glu Ser Val Lys Ser Arg Ile Thr Ile Asn Pro Asp Thr
                 85                  90                  95

Ser Lys Asn Gln Phe Ser Leu Gln Leu Asn Ser Val Thr Pro Glu Asp
                100                 105                 110

Thr Ala Val Tyr Tyr Cys Ala Arg Gly Asp Ser Ser Trp Tyr Ala
                115                 120                 125

Phe Asp Tyr Trp Gly Gln Gly Thr Leu Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445
```

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 15
<211> LENGTH: 214
<212> TYPE: PRT
<213> ORGANISM: Homo sapiens

<400> SEQUENCE: 15

Glu Ile Val Leu Thr Gln Ser Pro Gly Thr Leu Ser Leu Ser Leu Gly
1               5                   10                  15

Glu Arg Ala Thr Leu Ser Cys Arg Ala Ser Gln Ser Ile Ser Ser Ser
            20                  25                  30

Phe Leu Ala Trp Tyr Gln Gln Lys Pro Gly Gln Ala Pro Lys Leu Leu
        35                  40                  45

Ile Tyr Ala Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Leu
                85                  90                  95

Ser Phe Gly Gly Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 453
<212> TYPE: PRT
<213> ORGANISM: Homo sapiens

<400> SEQUENCE: 16

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Gly Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Asn His Asp Tyr Ala
    50                  55                  60

Glu Ser Val Lys Ser Arg Ile Thr Ile Asn Pro Asp Thr Ser Lys Asn
65                  70                  75                  80

```
Gln Phe Ser Leu Gln Leu Asn Ser Val Thr Pro Glu Asp Thr Ala Val
                85                  90                  95

Tyr Tyr Cys Ala Arg Gly Asp Ser Ser Ser Trp Tyr Ala Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 17
<211> LENGTH: 1363
<212> TYPE: PRT
<213> ORGANISM: Homo sapiens
```

<400> SEQUENCE: 17

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
    290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
        355                 360                 365

Tyr Lys Asp Gly Lys Ala Leu Ser Gly Arg His Ser Pro His Ala Leu
    370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415
```

-continued

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
    450                 455                 460

Pro Cys Lys Met Phe Ala Gln Arg Ser Leu Arg Arg Gln Gln Gln
465                 470                 475                 480

Asp Leu Met Pro Gln Cys Arg Asp Trp Arg Ala Val Thr Thr Gln Asp
                485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
    530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
    610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
    770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
        835                 840                 845

-continued

Arg Val Leu Gly Tyr Gly Ala Phe Gly Lys Val Val Glu Ala Ser Ala
850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
            995                 1000                1005

Leu Thr Met Glu Asp Leu Val Cys Tyr Ser Phe Gln Val Ala Arg
1010                1015                1020

Gly Met Glu Phe Leu Ala Ser Arg Lys Cys Ile His Arg Asp Leu
1025                1030                1035

Ala Ala Arg Asn Ile Leu Leu Ser Glu Ser Asp Val Val Lys Ile
1040                1045                1050

Cys Asp Phe Gly Leu Ala Arg Asp Ile Tyr Lys Asp Pro Asp Tyr
1055                1060                1065

Val Arg Lys Gly Ser Ala Arg Leu Pro Leu Lys Trp Met Ala Pro
1070                1075                1080

Glu Ser Ile Phe Asp Lys Val Tyr Thr Thr Gln Ser Asp Val Trp
1085                1090                1095

Ser Phe Gly Val Leu Leu Trp Glu Ile Phe Ser Leu Gly Ala Ser
1100                1105                1110

Pro Tyr Pro Gly Val Gln Ile Asn Glu Glu Phe Cys Gln Arg Leu
1115                1120                1125

Arg Asp Gly Thr Arg Met Arg Ala Pro Glu Leu Ala Thr Pro Ala
1130                1135                1140

Ile Arg Arg Ile Met Leu Asn Cys Trp Ser Gly Asp Pro Lys Ala
1145                1150                1155

Arg Pro Ala Phe Ser Glu Leu Val Glu Ile Leu Gly Asp Leu Leu
1160                1165                1170

Gln Gly Arg Gly Leu Gln Glu Glu Glu Val Cys Met Ala Pro
1175                1180                1185

Arg Ser Ser Gln Ser Ser Glu Glu Gly Ser Phe Ser Gln Val Ser
1190                1195                1200

Thr Met Ala Leu His Ile Ala Gln Ala Asp Ala Glu Asp Ser Pro
1205                1210                1215

Pro Ser Leu Gln Arg His Ser Leu Ala Ala Arg Tyr Tyr Asn Trp
1220                1225                1230

Val Ser Phe Pro Gly Cys Leu Ala Arg Gly Ala Glu Thr Arg Gly
1235                1240                1245

Ser Ser Arg Met Lys Thr Phe Glu Glu Phe Pro Met Thr Pro Thr
1250                1255                1260

-continued

| | | | | | | | | | | | |
|---|---|---|---|---|---|---|---|---|---|---|---|
|Thr|Tyr 1265|Lys|Gly|Ser|Val 1270|Asp|Asn|Gln|Thr 1275|Asp|Ser|Gly|Met|Val|

Thr Tyr Lys Gly Ser Val Asp Asn Gln Thr Asp Ser Gly Met Val
    1265            1270            1275

Leu Ala Ser Glu Glu Phe Glu Gln Ile Glu Ser Arg His Arg Gln
    1280            1285            1290

Glu Ser Gly Phe Ser Cys Lys Gly Pro Gly Gln Asn Val Ala Val
    1295            1300            1305

Thr Arg Ala His Pro Asp Ser Gln Gly Arg Arg Arg Pro Glu
    1310            1315            1320

Arg Gly Ala Arg Gly Gly Gln Val Phe Tyr Asn Ser Glu Tyr Gly
    1325            1330            1335

Glu Leu Ser Glu Pro Ser Glu Asp His Cys Ser Pro Ser Ala
    1340            1345            1350

Arg Val Thr Phe Phe Thr Asp Asn Ser Tyr
    1355            1360

<210> SEQ ID NO 18
<211> LENGTH: 1298
<212> TYPE: PRT
<213> ORGANISM: Homo sapiens

<400> SEQUENCE: 18

Met Gln Arg Gly Ala Ala Leu Cys Leu Arg Leu Trp Leu Cys Leu
1               5               10              15

Leu Leu Asp Gly Leu Val Ser Gly Tyr Ser Met Thr Pro Pro Thr Leu
            20              25              30

Asn Ile Thr Glu Glu Ser His Val Ile Asp Thr Gly Asp Ser Leu Ser
        35              40              45

Ile Ser Cys Arg Gly Gln His Pro Leu Glu Trp Ala Trp Pro Gly Ala
    50              55              60

Gln Glu Ala Pro Ala Thr Gly Asp Lys Asp Ser Glu Asp Thr Gly Val
65              70              75              80

Val Arg Asp Cys Glu Gly Thr Asp Ala Arg Pro Tyr Cys Lys Val Leu
                85              90              95

Leu Leu His Glu Val His Ala Asn Asp Thr Gly Ser Tyr Val Cys Tyr
            100             105             110

Tyr Lys Tyr Ile Lys Ala Arg Ile Glu Gly Thr Thr Ala Ala Ser Ser
        115             120             125

Tyr Val Phe Val Arg Asp Phe Glu Gln Pro Phe Ile Asn Lys Pro Asp
    130             135             140

Thr Leu Leu Val Asn Arg Lys Asp Ala Met Trp Val Pro Cys Leu Val
145             150             155             160

Ser Ile Pro Gly Leu Asn Val Thr Leu Arg Ser Gln Ser Ser Val Leu
                165             170             175

Trp Pro Asp Gly Gln Glu Val Val Trp Asp Asp Arg Arg Gly Met Leu
            180             185             190

Val Ser Thr Pro Leu Leu His Asp Ala Leu Tyr Leu Gln Cys Glu Thr
        195             200             205

Thr Trp Gly Asp Gln Asp Phe Leu Ser Asn Pro Phe Leu Val His Ile
    210             215             220

Thr Gly Asn Glu Leu Tyr Asp Ile Gln Leu Leu Pro Arg Lys Ser Leu
225             230             235             240

Glu Leu Leu Val Gly Glu Lys Leu Val Leu Asn Cys Thr Val Trp Ala
                245             250             255

Glu Phe Asn Ser Gly Val Thr Phe Asp Trp Asp Tyr Pro Gly Lys Gln
            260             265             270

-continued

```
Ala Glu Arg Gly Lys Trp Val Pro Glu Arg Arg Ser Gln Gln Thr His
        275                 280                 285
Thr Glu Leu Ser Ser Ile Leu Thr Ile His Asn Val Ser Gln His Asp
        290                 295                 300
Leu Gly Ser Tyr Val Cys Lys Ala Asn Asn Gly Ile Gln Arg Phe Arg
305                 310                 315                 320
Glu Ser Thr Glu Val Ile Val His Glu Asn Pro Phe Ile Ser Val Glu
                325                 330                 335
Trp Leu Lys Gly Pro Ile Leu Glu Ala Thr Ala Gly Asp Glu Leu Val
                340                 345                 350
Lys Leu Pro Val Lys Leu Ala Ala Tyr Pro Pro Pro Glu Phe Gln Trp
        355                 360                 365
Tyr Lys Asp Gly Lys Ala Leu Ser Gly Arg His Ser Pro His Ala Leu
        370                 375                 380
Val Leu Lys Glu Val Thr Glu Ala Ser Thr Gly Thr Tyr Thr Leu Ala
385                 390                 395                 400
Leu Trp Asn Ser Ala Ala Gly Leu Arg Arg Asn Ile Ser Leu Glu Leu
                405                 410                 415
Val Val Asn Val Pro Pro Gln Ile His Glu Lys Glu Ala Ser Ser Pro
                420                 425                 430
Ser Ile Tyr Ser Arg His Ser Arg Gln Ala Leu Thr Cys Thr Ala Tyr
        435                 440                 445
Gly Val Pro Leu Pro Leu Ser Ile Gln Trp His Trp Arg Pro Trp Thr
450                 455                 460
Pro Cys Lys Met Phe Ala Gln Arg Ser Leu Arg Arg Gln Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
                500                 505                 510
Gly Lys Asn Lys Thr Val Ser Lys Leu Val Ile Gln Asn Ala Asn Val
        515                 520                 525
Ser Ala Met Tyr Lys Cys Val Val Ser Asn Lys Val Gly Gln Asp Glu
        530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
                580                 585                 590
Leu Asn Leu Ser Thr Leu His Asp Ala His Gly Asn Pro Leu Leu Leu
        595                 600                 605
Asp Cys Lys Asn Val His Leu Phe Ala Thr Pro Leu Ala Ala Ser Leu
        610                 615                 620
Glu Glu Val Ala Pro Gly Ala Arg His Ala Thr Leu Ser Leu Ser Ile
625                 630                 635                 640
Pro Arg Val Ala Pro Glu His Glu Gly His Tyr Val Cys Glu Val Gln
                645                 650                 655
Asp Arg Arg Ser His Asp Lys His Cys His Lys Lys Tyr Leu Ser Val
                660                 665                 670
Gln Ala Leu Glu Ala Pro Arg Leu Thr Gln Asn Leu Thr Asp Leu Leu
        675                 680                 685
Val Asn Val Ser Asp Ser Leu Glu Met Gln Cys Leu Val Ala Gly Ala
        690                 695                 700
```

```
His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
        740                 745                 750

Ala Lys Gly Cys Val Asn Ser Ser Ala Ser Val Ala Val Glu Gly Ser
    755                 760                 765

Glu Asp Lys Gly Ser Met Glu Ile Val Ile Leu Val Gly Thr Gly Val
770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
        835                 840                 845

Arg Val Leu Gly Tyr Gly Ala Phe Gly Lys Val Val Glu Ala Ser Ala
    850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Asn Leu
            900                 905                 910

Leu Gly Ala Cys Thr Lys Pro Gln Gly Pro Leu Met Val Ile Val Glu
    915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
        995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125
```

```
Arg Asp Gly Thr Arg Met Arg Ala Pro Glu Leu Ala Thr Pro Ala
    1130            1135                1140

Ile Arg Arg Ile Met Leu Asn Cys Trp Ser Gly Asp Pro Lys Ala
    1145            1150                1155

Arg Pro Ala Phe Ser Glu Leu Val Glu Ile Leu Gly Asp Leu Leu
    1160            1165                1170

Gln Gly Arg Gly Leu Gln Glu Glu Glu Val Cys Met Ala Pro
    1175            1180                1185

Arg Ser Ser Gln Ser Ser Glu Glu Gly Ser Phe Ser Gln Val Ser
    1190            1195                1200

Thr Met Ala Leu His Ile Ala Gln Ala Asp Ala Glu Asp Ser Pro
    1205            1210                1215

Pro Ser Leu Gln Arg His Ser Leu Ala Ala Arg Tyr Tyr Asn Trp
    1220            1225                1230

Val Ser Phe Pro Gly Cys Leu Ala Arg Gly Ala Glu Thr Arg Gly
    1235            1240                1245

Ser Ser Arg Met Lys Thr Phe Glu Glu Phe Pro Met Thr Pro Thr
    1250            1255                1260

Thr Tyr Lys Gly Ser Val Asp Asn Gln Thr Asp Ser Gly Met Val
    1265            1270                1275

Leu Ala Ser Glu Glu Phe Glu Gln Ile Glu Ser Arg His Arg Gln
    1280            1285                1290

Glu Ser Gly Phe Arg
    1295

<210> SEQ ID NO 19
<211> LENGTH: 1363
<212> TYPE: PRT
<213> ORGANISM: Mus musculus

<400> SEQUENCE: 19

Met Gln Pro Gly Ala Ala Leu Asn Leu Arg Leu Trp Leu Cys Leu Gly
1               5                   10                  15

Leu Leu Gln Gly Leu Ala Asn Gly Tyr Ser Met Thr Pro Pro Thr Leu
                20                  25                  30

Asn Ile Thr Glu Asp Ser Tyr Val Ile Asp Thr Gly Asp Ser Leu Ser
            35                  40                  45

Ile Ser Cys Arg Gly Gln His Pro Leu Glu Trp Thr Trp Pro Gly Ala
    50                  55                  60

Gln Glu Val Leu Thr Thr Gly Lys Asp Ser Glu Asp Thr Arg Val
65              70                  75                  80

Val His Asp Cys Glu Gly Thr Glu Ala Arg Pro Tyr Cys Lys Val Leu
                85                  90                  95

Leu Leu Ala Gln Thr His Ala Asn Asn Thr Gly Ser Tyr His Cys Tyr
                100                 105                 110

Tyr Lys Tyr Ile Lys Ala Arg Ile Glu Gly Thr Thr Ala Ala Ser Thr
            115                 120                 125

Tyr Val Phe Val Arg Asp Phe Lys His Pro Phe Ile Asn Lys Pro Asp
    130                 135                 140

Thr Leu Leu Val Asn Arg Lys Asp Ser Met Trp Val Pro Cys Leu Val
145                 150                 155                 160

Ser Ile Pro Gly Leu Asn Ile Thr Leu Arg Ser Gln Ser Ser Ala Leu
                165                 170                 175

His Pro Asp Gly Gln Glu Val Leu Trp Asp Asp Arg Arg Gly Met Arg
                180                 185                 190
```

-continued

```
Val Pro Thr Gln Leu Leu Arg Asp Ala Leu Tyr Leu Gln Cys Glu Thr
        195                 200                 205

Thr Trp Gly Asp Gln Asn Phe Leu Ser Asn Leu Phe Val Val His Ile
210                 215                 220

Thr Gly Asn Glu Leu Tyr Asp Ile Gln Leu Tyr Pro Lys Lys Ser Met
225                 230                 235                 240

Glu Leu Leu Val Gly Glu Lys Leu Val Leu Asn Cys Thr Val Trp Ala
                245                 250                 255

Glu Phe Asp Ser Gly Val Thr Phe Asp Trp Asp Tyr Pro Gly Lys Gln
                260                 265                 270

Ala Glu Arg Ala Lys Trp Val Pro Glu Arg Arg Ser Gln Gln Thr His
        275                 280                 285

Thr Glu Leu Ser Ser Ile Leu Thr Ile His Asn Val Ser Gln Asn Asp
    290                 295                 300

Leu Gly Pro Tyr Val Cys Glu Ala Asn Asn Gly Ile Gln Arg Phe Arg
305                 310                 315                 320

Glu Ser Thr Glu Val Ile Val His Glu Lys Pro Phe Ile Ser Val Glu
                325                 330                 335

Trp Leu Lys Gly Pro Val Leu Glu Ala Thr Ala Gly Asp Glu Leu Val
                340                 345                 350

Lys Leu Pro Val Lys Leu Ala Ala Tyr Pro Pro Pro Glu Phe Gln Trp
        355                 360                 365

Tyr Lys Asp Arg Lys Ala Val Thr Gly Arg His Asn Pro His Ala Leu
    370                 375                 380

Val Leu Lys Glu Val Thr Glu Ala Ser Ala Gly Val Tyr Thr Leu Ala
385                 390                 395                 400

Leu Trp Asn Ser Ala Ala Gly Leu Arg Gln Asn Ile Ser Leu Glu Leu
                405                 410                 415

Val Val Asn Val Pro Pro His Ile His Glu Lys Glu Ala Ser Ser Pro
                420                 425                 430

Ser Ile Tyr Ser Arg His Ser Arg Gln Thr Leu Thr Cys Thr Ala Tyr
        435                 440                 445

Gly Val Pro Gln Pro Leu Ser Val Gln Trp His Trp Arg Pro Trp Thr
    450                 455                 460

Pro Cys Lys Thr Phe Ala Gln Arg Ser Leu Arg Arg Arg Gln Gln Arg
465                 470                 475                 480

Asp Gly Met Pro Gln Cys Arg Asp Trp Lys Glu Val Thr Thr Gln Asp
                485                 490                 495

Ala Val Asn Pro Ile Glu Ser Leu Asp Ser Trp Thr Glu Phe Val Glu
                500                 505                 510

Gly Lys Asn Lys Thr Val Ser Lys Leu Val Ile Gln Asp Ala Asn Val
        515                 520                 525

Ser Ala Met Tyr Lys Cys Val Val Asn Lys Val Gly Gln Asp Glu
    530                 535                 540

Arg Leu Ile Tyr Phe Tyr Val Thr Thr Ile Pro Asp Gly Phe Ser Ile
545                 550                 555                 560

Glu Ser Glu Pro Ser Glu Asp Pro Leu Glu Gly Gln Ser Val Arg Leu
                565                 570                 575

Ser Cys Arg Ala Asp Asn Tyr Thr Tyr Glu His Leu Arg Trp Tyr Arg
                580                 585                 590

Leu Asn Leu Ser Thr Leu His Asp Ala Gln Gly Asn Pro Leu Leu Leu
        595                 600                 605

Asp Cys Lys Asn Val His Leu Phe Ala Thr Pro Leu Glu Ala Asn Leu
    610                 615                 620
```

-continued

Glu Glu Ala Glu Pro Gly Ala Arg His Ala Thr Leu Ser Leu Asn Ile
625                 630                 635                 640

Pro Arg Val Ala Pro Glu Asp Glu Gly Asp Tyr Val Cys Glu Val Gln
            645                 650                 655

Asp Arg Arg Ser Gln Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Arg Cys Pro Val Ala Gly Ala
690                 695                 700

His Val Pro Ser Ile Val Trp Tyr Lys Asp Glu Arg Leu Leu Glu Lys
705                 710                 715                 720

Glu Ser Gly Ile Asp Leu Ala Asp Ser Asn Gln Arg Leu Ser Ile Gln
            725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Ile Gly Thr Gly Val
770                 775                 780

Ile Ala Val Phe Phe Trp Val Leu Leu Leu Leu Ile Phe Cys Asn Met
785                 790                 795                 800

Lys Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
        820                 825                 830

Tyr Asp Ala Ser Gln Trp Glu Phe Pro Arg Glu Arg Leu His Leu Gly
        835                 840                 845

Arg Val Leu Gly His Gly Ala Phe Gly Lys Val Val Glu Ala Ser Ala
850                 855                 860

Phe Gly Ile Asn Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
        900                 905                 910

Leu Gly Ala Cys Thr Lys Pro Asn Gly Pro Leu Met Val Ile Val Glu
        915                 920                 925

Phe Cys Lys Tyr Gly Asn Leu Ser Asn Phe Leu Arg Val Lys Arg Asp
930                 935                 940

Thr Phe Asn Pro Tyr Ala Glu Lys Ser Pro Glu Gln Arg Arg Arg Phe
945                 950                 955                 960

Arg Ala Met Val Glu Gly Ala Lys Ala Asp Arg Arg Arg Pro Gly Ser
            965                 970                 975

Ser Asp Arg Ala Leu Phe Thr Arg Phe Leu Met Gly Lys Gly Ser Ala
            980                 985                 990

Arg Arg Ala Pro Leu Val Gln Glu Ala Glu Asp Leu Trp Leu Ser Pro
        995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Ile Val Lys Ile
    1040                1045                1050

```
Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Lys Asp Gly Thr Arg Met Arg Ala Pro Glu Leu Ala Thr Pro Ala
    1130                1135                1140

Ile Arg His Ile Met Gln Ser Cys Trp Ser Gly Asp Pro Lys Ala
    1145                1150                1155

Arg Pro Ala Phe Ser Asp Leu Val Glu Ile Leu Gly Asp Leu Leu
    1160                1165                1170

Gln Gly Gly Gly Trp Gln Glu Glu Glu Glu Arg Met Ala Leu
    1175                1180                1185

His Ser Ser Gln Ser Ser Glu Asp Gly Phe Met Gln Ala Ser
    1190                1195                1200

Thr Thr Ala Leu His Ile Thr Glu Ala Asp Ala Asp Ser Pro
    1205                1210                1215

Pro Ser Met His Cys His Ser Leu Ala Ala Arg Tyr Tyr Asn Cys
    1220                1225                1230

Val Ser Phe Pro Gly Arg Leu Ala Arg Gly Thr Lys Thr Pro Gly
    1235                1240                1245

Ser Ser Arg Met Lys Thr Phe Glu Glu Leu Pro Met Thr Pro Thr
    1250                1255                1260

Thr Tyr Lys Ala Ser Met Asp Asn Gln Thr Asp Ser Gly Met Val
    1265                1270                1275

Leu Ala Ser Glu Glu Phe Glu Glu Leu Glu Ser Arg His Arg Pro
    1280                1285                1290

Glu Gly Ser Phe Ser Cys Lys Gly Pro Gly Gln His Met Asp Ile
    1295                1300                1305

Pro Arg Gly His Pro Asp Pro Gln Gly Arg Arg Arg Pro Thr
    1310                1315                1320

Gln Gly Ala Gln Gly Gly Lys Val Phe Tyr Asn Asn Glu Tyr Gly
    1325                1330                1335

Glu Val Ser Gln Pro Cys Thr Glu Gly Asp Cys Cys Pro Ser Ala
    1340                1345                1350

Gly Ser Thr Phe Phe Ala Asp Ser Ser Tyr
    1355                1360

<210> SEQ ID NO 20
<211> LENGTH: 1363
<212> TYPE: PRT
<213> ORGANISM: Mus musculus

<400> SEQUENCE: 20

Met Gln Pro Gly Ala Ala Leu Asn Leu Arg Leu Trp Leu Cys Leu Gly
1               5                   10                  15

Leu Leu Gln Gly Leu Ala Asn Gly Tyr Ser Met Thr Pro Pro Thr Leu
                20                  25                  30

Asn Ile Thr Glu Asp Ser Tyr Val Ile Asp Thr Gly Asp Ser Leu Ser
            35                  40                  45
```

-continued

```
Ile Ser Cys Arg Gly Gln His Pro Leu Glu Trp Thr Trp Pro Gly Ala
    50                  55                  60
Gln Glu Val Leu Thr Thr Gly Gly Lys Asp Ser Glu Asp Thr Arg Val
65                  70                  75                  80
Val His Asp Cys Glu Gly Thr Glu Ala Arg Pro Tyr Cys Lys Val Leu
                    85                  90                  95
Leu Leu Ala Gln Thr His Ala Asn Asn Thr Gly Ser Tyr His Cys Tyr
                100                 105                 110
Tyr Lys Tyr Ile Lys Ala Arg Ile Glu Gly Thr Thr Ala Ala Ser Thr
            115                 120                 125
Tyr Val Phe Val Arg Asp Phe Lys His Pro Phe Ile Asn Lys Pro Asp
        130                 135                 140
Thr Leu Leu Val Asn Arg Lys Asp Ser Met Trp Val Pro Cys Leu Val
145                 150                 155                 160
Ser Ile Pro Gly Leu Asn Ile Thr Leu Arg Ser Gln Ser Ser Ala Leu
                    165                 170                 175
His Pro Asp Gly Gln Glu Val Leu Trp Asp Asp Arg Arg Gly Met Arg
                180                 185                 190
Val Pro Thr Gln Leu Leu Arg Asp Ala Leu Tyr Leu Gln Cys Glu Thr
            195                 200                 205
Thr Trp Gly Asp Gln Asn Phe Leu Ser Asn Pro Phe Val Val His Ile
        210                 215                 220
Thr Gly Asn Glu Leu Tyr Asp Ile Gln Leu Tyr Pro Lys Lys Ser Met
225                 230                 235                 240
Glu Leu Leu Val Gly Lys Leu Val Leu Asn Cys Thr Val Trp Ala
                    245                 250                 255
Glu Phe Asp Ser Gly Val Thr Phe Asp Trp Asp Tyr Pro Gly Lys Gln
                260                 265                 270
Ala Glu Arg Ala Lys Trp Val Pro Glu Arg Arg Ser Gln Gln Thr His
            275                 280                 285
Thr Glu Leu Ser Ser Ile Leu Thr Ile His Asn Val Ser Gln Asn Asp
        290                 295                 300
Leu Gly Pro Tyr Val Cys Glu Ala Asn Asn Gly Ile Gln Arg Phe Arg
305                 310                 315                 320
Glu Ser Thr Glu Val Ile Val His Glu Lys Pro Phe Ile Ser Val Glu
                    325                 330                 335
Trp Leu Lys Gly Pro Val Leu Glu Ala Thr Ala Gly Asp Glu Leu Val
                340                 345                 350
Lys Leu Pro Val Lys Leu Ala Ala Tyr Pro Pro Glu Phe Gln Trp
            355                 360                 365
Tyr Lys Asp Arg Lys Ala Val Thr Gly Arg His Asn Pro His Ala Leu
        370                 375                 380
Val Leu Lys Glu Val Thr Glu Ala Ser Ala Gly Val Tyr Thr Leu Ala
385                 390                 395                 400
Leu Trp Asn Ser Ala Ala Gly Leu Arg Gln Asn Ile Ser Leu Glu Leu
                    405                 410                 415
Val Val Asn Val Pro His Ile His Glu Lys Glu Ala Ser Ser Pro
                420                 425                 430
Ser Ile Tyr Ser Arg His Ser Arg Gln Thr Leu Thr Cys Thr Ala Tyr
            435                 440                 445
Gly Val Pro Gln Pro Leu Ser Val Gln Trp His Trp Arg Pro Trp Thr
        450                 455                 460
Pro Cys Lys Thr Phe Ala Gln Arg Ser Leu Arg Arg Gln Gln Arg
465                 470                 475                 480
```

```
Asp Gly Met Pro Gln Cys Arg Asp Trp Lys Glu Val Thr Thr Gln Asp
                485                 490                 495
Ala Val Asn Pro Ile Glu Ser Leu Asp Ser Trp Thr Glu Phe Val Glu
            500                 505                 510
Gly Lys Asn Lys Thr Val Ser Lys Leu Val Ile Gln Asp Ala Asn Val
        515                 520                 525
Ser Ala Met Tyr Lys Cys Val Val Asn Lys Val Gly Gln Asp Glu
    530                 535                 540
Arg Leu Ile Tyr Phe Tyr Val Thr Thr Ile Pro Asp Gly Phe Ser Ile
545                 550                 555                 560
Glu Ser Glu Pro Ser Glu Asp Pro Leu Glu Gly Gln Ser Val Arg Leu
                565                 570                 575
Ser Cys Arg Ala Asp Asn Tyr Thr Tyr Glu His Leu Arg Trp Tyr Arg
            580                 585                 590
Leu Asn Leu Ser Thr Leu His Asp Ala Gln Gly Asn Pro Leu Leu Leu
        595                 600                 605
Asp Cys Lys Asn Val His Leu Phe Ala Thr Pro Leu Glu Ala Asn Leu
    610                 615                 620
Glu Glu Ala Glu Pro Gly Ala Arg His Ala Thr Leu Ser Leu Asn Ile
625                 630                 635                 640
Pro Arg Val Ala Pro Glu Asp Glu Gly Asp Tyr Val Cys Glu Val Gln
                645                 650                 655
Asp Arg Arg Ser Gln Asp Lys His Cys His Lys Lys Tyr Leu Ser Val
            660                 665                 670
Gln Ala Leu Glu Ala Pro Arg Leu Thr Gln Asn Leu Thr Asp Leu Leu
        675                 680                 685
Val Asn Val Ser Asp Ser Leu Glu Met Arg Cys Pro Val Ala Gly Ala
    690                 695                 700
His Val Pro Ser Ile Val Trp Tyr Lys Asp Glu Arg Leu Leu Glu Lys
705                 710                 715                 720
Glu Ser Gly Ile Asp Leu Ala Asp Ser Asn Gln Arg Leu Ser Ile Gln
                725                 730                 735
Arg Val Arg Glu Glu Asp Ala Gly Arg Tyr Leu Cys Ser Val Cys Asn
            740                 745                 750
Ala Lys Gly Cys Val Asn Ser Ser Ala Ser Val Ala Val Glu Gly Ser
        755                 760                 765
Glu Asp Lys Gly Ser Met Glu Ile Val Ile Leu Ile Gly Thr Gly Val
    770                 775                 780
Ile Ala Val Phe Phe Trp Val Leu Leu Leu Leu Ile Phe Cys Asn Met
785                 790                 795                 800
Lys Arg Pro Ala His Ala Asp Ile Lys Thr Gly Tyr Leu Ser Ile Ile
                805                 810                 815
Met Asp Pro Gly Glu Val Pro Leu Glu Glu Gln Cys Glu Tyr Leu Ser
            820                 825                 830
Tyr Asp Ala Ser Gln Trp Glu Phe Pro Arg Glu Arg Leu His Leu Gly
        835                 840                 845
Arg Val Leu Gly His Gly Ala Phe Gly Lys Val Val Glu Ala Ser Ala
    850                 855                 860
Phe Gly Ile Asn Lys Gly Ser Ser Cys Asp Thr Val Ala Val Lys Met
865                 870                 875                 880
Leu Lys Glu Gly Ala Thr Ala Ser Glu His Arg Ala Leu Met Ser Glu
                885                 890                 895
Leu Lys Ile Leu Ile His Ile Gly Asn His Leu Asn Val Val Asn Leu
            900                 905                 910
```

-continued

Leu Gly Ala Cys Thr Lys Pro Asn Gly Pro Leu Met Val Ile Val Glu
            915                 920                 925

Phe Cys Lys Tyr Gly Asn Leu Ser Asn Phe Leu Arg Val Lys Arg Asp
930                 935                 940

Thr Phe Asn Pro Tyr Ala Glu Lys Ser Pro Glu Gln Arg Arg Phe
945                 950                 955                 960

Arg Ala Met Val Glu Gly Ala Lys Ala Asp Arg Arg Arg Pro Gly Ser
            965                 970                 975

Ser Asp Arg Ala Leu Phe Thr Arg Phe Leu Met Gly Lys Gly Ser Ala
            980                 985                 990

Arg Arg Ala Pro Leu Val Gln Glu Ala Glu Asp Leu Trp Leu Ser Pro
            995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Ile Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Lys Asp Gly Thr Arg Met Arg Ala Pro Glu Leu Ala Thr Pro Ala
    1130                1135                1140

Ile Arg His Ile Met Gln Ser Cys Trp Ser Gly Asp Pro Lys Ala
    1145                1150                1155

Arg Pro Ala Phe Ser Asp Leu Val Glu Ile Leu Gly Asp Leu Leu
    1160                1165                1170

Gln Gly Gly Gly Trp Gln Glu Glu Glu Glu Arg Met Ala Leu
    1175                1180                1185

His Ser Ser Gln Ser Ser Glu Glu Asp Gly Phe Met Gln Ala Ser
    1190                1195                1200

Thr Thr Ala Leu His Ile Thr Glu Ala Asp Ala Asp Asp Ser Pro
    1205                1210                1215

Pro Ser Met His Cys His Ser Leu Ala Ala Arg Tyr Tyr Asn Cys
    1220                1225                1230

Val Ser Phe Pro Gly Arg Leu Ala Arg Gly Thr Lys Thr Pro Gly
    1235                1240                1245

Ser Ser Arg Met Lys Thr Phe Glu Glu Leu Pro Met Thr Pro Thr
    1250                1255                1260

Thr Tyr Lys Ala Ser Met Asp Asn Gln Thr Asp Ser Gly Met Val
    1265                1270                1275

Leu Ala Ser Glu Glu Phe Glu Leu Glu Ser Arg His Arg Pro
    1280                1285                1290

Glu Gly Ser Phe Ser Cys Lys Gly Pro Gly Gln His Met Asp Ile
    1295                1300                1305

Pro Arg Gly His Pro Asp Pro Gln Gly Arg Arg Arg Pro Thr
    1310                1315                1320

-continued

Gln Gly Ala Gln Gly Gly Lys Val Phe Tyr Asn Asn Glu Tyr Gly
    1325                1330                1335

Glu Val Ser Gln Pro Cys Thr Glu Gly Asp Cys Cys Pro Ser Ala
    1340                1345                1350

Gly Ser Thr Phe Phe Ala Asp Ser Ser Tyr
    1355                1360

<210> SEQ ID NO 21
<211> LENGTH: 1363
<212> TYPE: PRT
<213> ORGANISM: Mus musculus

<400> SEQUENCE: 21

Met Gln Pro Gly Ala Ala Leu Asn Leu Arg Leu Trp Leu Cys Leu Gly
1               5                   10                  15

Leu Leu Gln Gly Leu Ala Asn Gly Tyr Ser Met Thr Pro Pro Thr Leu
            20                  25                  30

Asn Ile Thr Glu Asp Ser Tyr Val Ile Asp Thr Gly Asp Ser Leu Ser
        35                  40                  45

Ile Ser Cys Arg Gly Gln His Pro Leu Glu Trp Thr Trp Pro Gly Ala
    50                  55                  60

Gln Glu Val Leu Thr Thr Gly Gly Lys Asp Ser Glu Asp Thr Arg Val
65                  70                  75                  80

Val His Asp Cys Glu Gly Thr Glu Ala Arg Pro Tyr Cys Lys Val Leu
                85                  90                  95

Leu Leu Ala Gln Thr His Ala Asn Asn Thr Gly Ser Tyr His Cys Tyr
            100                 105                 110

Tyr Lys Tyr Ile Lys Ala Arg Ile Glu Gly Thr Thr Ala Ala Ser Thr
        115                 120                 125

Tyr Val Phe Val Arg Asp Phe Lys His Pro Phe Ile Asn Lys Pro Asp
    130                 135                 140

Thr Leu Leu Val Asn Arg Lys Asp Ser Met Trp Val Pro Cys Leu Val
145                 150                 155                 160

Ser Ile Pro Gly Leu Asn Ile Thr Leu Arg Ser Gln Ser Ser Val Leu
                165                 170                 175

His Pro Asp Gly Gln Glu Val Leu Trp Asp Asp Arg Arg Gly Met Arg
            180                 185                 190

Val Pro Thr Gln Leu Leu Arg Asp Ala Leu Tyr Leu Gln Cys Glu Thr
        195                 200                 205

Thr Trp Gly Asp Gln Asn Phe Leu Ser Asn Leu Phe Val Val His Ile
    210                 215                 220

Thr Gly Asn Glu Leu Tyr Asp Ile Gln Leu Tyr Pro Lys Lys Ser Met
225                 230                 235                 240

Glu Leu Leu Val Gly Glu Lys Leu Val Leu Asn Cys Thr Val Trp Ala
                245                 250                 255

Glu Phe Asp Ser Gly Val Thr Phe Asp Trp Asp Tyr Pro Gly Lys Gln
            260                 265                 270

Ala Glu Arg Ala Lys Trp Val Pro Glu Arg Arg Ser Gln Gln Thr His
        275                 280                 285

Thr Glu Leu Ser Ser Ile Leu Thr Ile His Asn Val Ser Gln Asn Asp
    290                 295                 300

Leu Gly Pro Tyr Val Cys Glu Ala Asn Asn Gly Ile Gln Arg Phe Arg
305                 310                 315                 320

Glu Ser Thr Glu Val Ile Val His Glu Lys Pro Phe Ile Ser Val Glu
                325                 330                 335

```
Trp Leu Lys Gly Pro Val Leu Glu Ala Thr Ala Gly Asp Glu Leu Val
            340                 345                 350

Lys Leu Pro Val Lys Leu Ala Ala Tyr Pro Pro Glu Phe Gln Trp
        355                 360                 365

Tyr Lys Asp Arg Lys Ala Val Thr Gly Arg His Asn Pro His Ala Leu
        370                 375                 380

Val Leu Lys Glu Val Thr Glu Ala Ser Ala Gly Val Tyr Thr Leu Ala
385                 390                 395                 400

Leu Trp Asn Ser Ala Ala Gly Leu Arg Gln Asn Ile Ser Leu Glu Leu
                405                 410                 415

Val Val Asn Val Pro Pro His Ile His Glu Lys Glu Ala Ser Ser Pro
            420                 425                 430

Ser Ile Tyr Ser Arg His Ser Arg Gln Thr Leu Thr Cys Thr Ala Tyr
        435                 440                 445

Gly Val Pro Gln Pro Leu Ser Val Gln Trp His Trp Arg Pro Trp Thr
        450                 455                 460

Pro Cys Lys Thr Phe Ala Gln Arg Ser Leu Arg Arg Gln Gln Arg
465                 470                 475                 480

Asp Gly Met Pro Gln Cys Arg Asp Trp Lys Glu Val Thr Thr Gln Asp
                485                 490                 495

Ala Val Asn Pro Ile Glu Ser Leu Asp Ser Trp Thr Glu Phe Val Glu
            500                 505                 510

Gly Lys Asn Lys Thr Val Ser Lys Leu Val Ile Gln Asp Ala Asn Val
        515                 520                 525

Ser Ala Met Tyr Lys Cys Val Val Asn Lys Val Gly Gln Asp Glu
        530                 535                 540

Arg Leu Ile Tyr Phe Tyr Val Thr Thr Ile Pro Asp Gly Phe Ser Ile
545                 550                 555                 560

Glu Ser Glu Pro Ser Glu Asp Pro Leu Glu Gly Gln Ser Val Arg Leu
                565                 570                 575

Ser Cys Arg Ala Asp Asn Tyr Thr Tyr Glu His Leu Arg Trp Tyr Arg
                580                 585                 590

Leu Asn Leu Ser Thr Leu His Asp Ala Gln Gly Asn Pro Leu Leu Leu
        595                 600                 605

Asp Cys Lys Asn Val His Leu Phe Ala Thr Pro Leu Glu Ala Asn Leu
        610                 615                 620

Glu Glu Ala Glu Pro Gly Ala Arg His Ala Thr Leu Ser Leu Asn Ile
625                 630                 635                 640

Pro Arg Val Ala Pro Glu Asp Glu Gly Asp Tyr Val Cys Glu Val Gln
                645                 650                 655

Asp Arg Arg Ser Gln Asp Lys His Cys His Lys Lys Tyr Leu Ser Val
                660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Arg Cys Pro Val Ala Gly Ala
            690                 695                 700

His Val Pro Ser Ile Val Trp Tyr Lys Asp Glu Arg Leu Leu Glu Lys
705                 710                 715                 720

Glu Ser Gly Ile Asp Leu Ala Asp Ser Asn Gln Arg Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765
```

-continued

Glu Asp Lys Gly Ser Met Glu Ile Val Ile Leu Ile Gly Thr Gly Val
770             775                 780
Ile Ala Val Phe Phe Trp Val Leu Leu Leu Ile Phe Cys Asn Met
785                 790                 795                 800
Lys Arg Pro Ala His Ala Asp Ile Lys Thr Gly Tyr Leu Ser Ile Ile
            805                 810                 815
Met Asp Pro Gly Glu Val Pro Leu Glu Glu Gln Cys Glu Tyr Leu Ser
        820                 825                 830
Tyr Asp Ala Ser Gln Trp Glu Phe Pro Arg Glu Arg Leu His Leu Gly
        835                 840                 845
Arg Val Leu Gly His Gly Ala Phe Gly Lys Val Glu Ala Ser Ala
    850                 855                 860
Phe Gly Ile Asn Lys Gly Ser Ser Cys Asp Thr Val Ala Val Lys Met
865                 870                 875                 880
Leu Lys Glu Gly Ala Thr Ala Ser Glu His Arg Ala Leu Met Ser Glu
            885                 890                 895
Leu Lys Ile Leu Ile His Ile Gly Asn His Leu Asn Val Val Asn Leu
        900                 905                 910
Leu Gly Ala Cys Thr Lys Pro Asn Gly Pro Leu Met Val Ile Val Glu
        915                 920                 925
Phe Cys Lys Tyr Gly Asn Leu Ser Asn Phe Leu Arg Val Lys Arg Asp
930                 935                 940
Thr Phe Asn Pro Tyr Ala Glu Lys Ser Pro Glu Gln Arg Arg Arg Phe
945                 950                 955                 960
Arg Ala Met Val Glu Gly Ala Lys Ala Asp Arg Arg Pro Gly Ser
            965                 970                 975
Ser Asp Arg Ala Leu Phe Thr Arg Phe Leu Met Gly Lys Gly Ser Ala
        980                 985                 990
Arg Arg Ala Pro Leu Val Gln Glu  Ala Glu Asp Leu Trp  Leu Ser Pro
        995                 1000                1005
Leu Thr  Met Glu Asp Leu Val  Cys Tyr Ser Phe Gln  Val Ala Arg
    1010                1015                1020
Gly Met  Glu Phe Leu Ala Ser  Arg Lys Cys Ile His  Arg Asp Leu
    1025                1030                1035
Ala Ala  Arg Asn Ile Leu Leu  Ser Glu Ser Asp Ile  Val Lys Ile
    1040                1045                1050
Cys Asp  Phe Gly Leu Ala Arg  Asp Ile Tyr Lys Asp  Pro Asp Tyr
    1055                1060                1065
Val Arg  Lys Gly Ser Ala Arg  Leu Pro Leu Lys Trp  Met Ala Pro
    1070                1075                1080
Glu Ser  Ile Phe Asp Lys Val  Tyr Thr Thr Gln Ser  Asp Val Trp
    1085                1090                1095
Ser Phe  Gly Val Leu Leu Trp  Glu Ile Phe Ser Leu  Gly Ala Ser
    1100                1105                1110
Pro Tyr  Pro Gly Val Gln Ile  Asn Glu Glu Phe Cys  Gln Arg Leu
    1115                1120                1125
Lys Asp  Gly Thr Arg Met Arg  Ala Pro Glu Leu Ala  Thr Pro Ala
    1130                1135                1140
Ile Arg  His Ile Met Gln Ser  Cys Trp Ser Gly Asp  Pro Lys Ala
    1145                1150                1155
Arg Pro  Ala Phe Ser Asp Leu  Val Glu Ile Leu Gly  Asp Leu Leu
    1160                1165                1170
Gln Gly  Gly Gly Trp Gln Glu  Glu Glu Glu Glu Arg  Met Ala Leu
    1175                1180                1185

```
His Ser Ser Gln Ser Ser Glu Glu Asp Gly Phe Met Gln Ala Ser
    1190            1195                1200

Thr Thr Ala Leu His Ile Thr Glu Ala Asp Ala Asp Asp Ser Pro
    1205            1210                1215

Pro Ser Met His Cys His Ser Leu Ala Ala Arg Tyr Tyr Asn Cys
    1220            1225                1230

Val Ser Phe Pro Gly Arg Leu Ala Arg Gly Thr Lys Thr Pro Gly
    1235            1240                1245

Ser Ser Arg Met Lys Thr Phe Glu Glu Leu Pro Met Thr Pro Thr
    1250            1255                1260

Thr Tyr Lys Ala Ser Met Asp Asn Gln Thr Asp Ser Gly Met Val
    1265            1270                1275

Leu Ala Ser Glu Glu Phe Glu Leu Glu Ser Arg His Arg Pro
    1280            1285                1290

Glu Gly Ser Phe Ser Cys Lys Gly Pro Gly Gln His Met Asp Ile
    1295            1300                1305

Pro Arg Gly His Pro Asp Pro Gln Gly Arg Arg Arg Arg Pro Thr
    1310            1315                1320

Gln Gly Ala Gln Gly Gly Lys Val Phe Tyr Asn Asn Glu Tyr Gly
    1325            1330                1335

Glu Val Ser Gln Pro Cys Thr Glu Gly Asp Cys Cys Pro Ser Ala
    1340            1345                1350

Gly Ser Thr Phe Phe Ala Asp Ser Ser Tyr
    1355            1360

<210> SEQ ID NO 22
<211> LENGTH: 113
<212> TYPE: PRT
<213> ORGANISM: Homo sapiens

<400> SEQUENCE: 22

Thr Glu Glu Thr Ile Lys Phe Ala Ala Ala His Tyr Asn Thr Glu Ile
1               5                   10                  15

Leu Lys Ser Ile Asp Asn Glu Trp Arg Lys Thr Gln Cys Met Pro Arg
            20                  25                  30

Glu Val Cys Ile Asp Val Gly Lys Glu Phe Gly Val Ala Thr Asn Thr
        35                  40                  45

Phe Phe Lys Pro Pro Cys Val Ser Val Tyr Arg Cys Gly Gly Cys Cys
    50                  55                  60

Asn Ser Glu Gly Leu Gln Cys Met Asn Thr Ser Thr Ser Tyr Leu Ser
65                  70                  75                  80

Lys Thr Leu Phe Glu Ile Thr Val Pro Leu Ser Gln Gly Pro Lys Pro
                85                  90                  95

Val Thr Ile Ser Phe Ala Asn His Thr Ser Cys Arg Cys Met Ser Lys
            100                 105                 110

Leu
```